United States Patent
Estell

(10) Patent No.: US 6,642,011 B2
(45) Date of Patent: *Nov. 4, 2003

(54) HUMAN PROTEASE AND USE OF SUCH PROTEASE FOR PHARMACEUTICAL APPLICATIONS AND FOR REDUCING THE ALLERGENICITY OF NON-HUMAN PROTEINS

(75) Inventor: David A. Estell, San Mateo, CA (US)

(73) Assignee: Genencor International, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/060,854

(22) Filed: Apr. 15, 1998

(65) Prior Publication Data

US 2002/0081703 A1 Jun. 27, 2002

(51) Int. Cl.[7] .......................... G01N 33/53; C12Q 1/37; C12N 15/74
(52) U.S. Cl. .......................... 435/7.24; 435/23; 435/471
(58) Field of Search .................... 435/220, 221, 435/222, 226, 69.1, 471, 252.3, 252.35, 320.1, 7.1, 7.6; 536/23.2

(56) References Cited

U.S. PATENT DOCUMENTS

| | | | |
|---|---|---|---|
| 4,261,868 A | 4/1981 | Hora et al. | 252/529 |
| 4,404,128 A | 9/1983 | Anderson | 252/546 |
| 4,533,359 A | 8/1985 | Kondo et al. | 8/128 R |
| 4,760,025 A | 7/1988 | Estell et al. | 435/222 |
| 4,914,031 A | 4/1990 | Zukowski et al. | 435/222 |
| 5,147,642 A | 9/1992 | Lotz et al. | 424/94.61 |
| 5,155,033 A | 10/1992 | Estell et al. | 435/221 |

(List continued on next page.)

FOREIGN PATENT DOCUMENTS

| | | |
|---|---|---|
| EP | 0 134 267 | 8/1989 |
| EP | 0 328 229 B1 | 1/1994 |
| EP | 2 251 446 A1 * | 1/1998 |
| WO | WO 89/06279 | 7/1989 |
| WO | WO 92/10755 | 6/1992 |
| WO | WO 92/10755 A | 6/1992 |
| WO | WO 92/11794 A | 6/1993 |
| WO | WO 94/10191 | 5/1994 |
| WO | WO 96/17929 | 6/1996 |
| WO | WO 96/34946 A1 * | 11/1996 |
| WO | WO 96/40791 | 12/1996 |
| WO | WO 97/30148 | 8/1997 |
| WO | WO 99/53038 A | 10/1999 |

OTHER PUBLICATIONS

Nagase, T., et a., DNA Research, vol. 2, "Prediction of the coding sequences of unidentified human genes. III. The coding sequences of 40 new genes deduced by analysis cDNA clones from human cell line KG–1." 1995.*

(List continued on next page.)

Primary Examiner—Ponnathapu Achutamurthy
Assistant Examiner—William W. Moore
(74) Attorney, Agent, or Firm—Genencor International, Inc.

(57) ABSTRACT

The present invention relates to a method of producing novel improved protein mutant which produce low allergenic response in humans compared to the parent of that mutant. Specifically, the present invention comprises neutralizing or reducing the allergenicity of a protein by introducing therein as replacement or modification of an epitope on such protein a sequence from human subtilisin.

15 Claims, 16 Drawing Sheets

U.S. PATENT DOCUMENTS

| | | | |
|---|---|---|---|
| 5,182,204 A | | 1/1993 | Estell et al. ................ 435/222 |
| 5,185,258 A | | 2/1993 | Caldwell et al. ............ 435/220 |
| 5,204,015 A | | 4/1993 | Caldwell et al. ....... 252/174.12 |
| 5,264,366 A | | 11/1993 | Ferrari et al. .......... 435/252.31 |
| 5,314,692 A | | 5/1994 | Haarasilta et al. ......... 424/94.2 |
| 5,460,950 A | * | 10/1995 | Barr et al. ................. 435/69.1 |
| 5,612,055 A | | 3/1997 | Bedford et al. ............. 424/442 |
| 5,766,898 A | * | 6/1998 | Loevborg ................... 435/471 |
| 5,801,038 A | * | 9/1998 | Bott et al. .................. 435/221 |
| 5,837,517 A | * | 11/1998 | Sierkstra et al. ............ 435/221 |
| 5,840,299 A | * | 11/1998 | Bendig et al. ........... 424/133.1 |
| 5,858,357 A | * | 1/1999 | Trnka et al. ............. 424/96.64 |
| 5,863,756 A | * | 1/1999 | Barr et al. ................. 435/69.1 |

OTHER PUBLICATIONS

Nagase, T., et al., EMBL database Accession No. Q14703, "cDNA sequence encoding KIAA0091 protein/subtilase" translated as amino acid sequence, one page, 1996.*

Drenth, Jan et al. << Subtilisin Novo—The Three–Dimensional Structure and Its Comparision with Subsilisin BPN, >> Eur. J. Biochem. vol. 26, pp. 177–181, 1972.

<<Kraut, Joseph, << Serine Proteases : Structure and Mechanism of Catalysis, >> Ann. Rev. Biochem., vol. 46, pp. 331–358, 1977.

*Moeller, G. ed., << Antigenic Requirements for Activation of MHC–Restricted Responses, >> Immunological Review, vol. 98, p. 187, Copenhagen, Munksgaard, 1987.

Philipp, M., et al., << Kinetics of subtilisin and thiolsubtilisin, >> Mol. Cell. Biochem., vol. 51, pp. 5–32, 1983.

Polgar, Laszlo et al., << Peptic Peptide of Thiolsubtilisin— Analytical Evidence for the Chemical Transformation of the Essential Serine–221 to Cysteine–221, >> Biochimica et Biophysica Acta, vol. 667, pp. 351–354, 1981.

Poulos, Thomas L., et al., << Polypeptide Halomethyl Ketones Bind to Serine Proteases as Analogs of the Tetrahedral Intermediate, >> The Journal of Biological Chemistry, vol. 251, pp. 1097–1103, 1976.

Robertus, Jon D. et al., << An X–ray Crystallographic Study of the Binding of Peptide Chloromethyl ketone Inhibitors to Subtilisin BPN >> Biochemistry, vol. 11, No. 13, pp. 2439–2449, 1972.

Smeekens, Steven P. et al., << Identification of a Human Insulinoma cDNA Encoding a Novel Mammalian Protein Structurally Related to the Yeast Dibasic Processing Protease Kex2, >> The Journal of Biological Chemistry, vol. 265, No. 6, pp. 2997–3000, 1990.

Stauffer, C.E., et al., << The Effect on Subtilisian Activity of Oxidizing a Methionine Residue, >> The Journal of Biological Chemistry, vol. 244, No. 19, pp. 5333–5338, 1969.

Stroud, Robert M., << A Family of Protein–Cutting Proteins, >> R. Sci. Amer., vol. 131, pp. 74–88.

Svendsen, I.B., << Chemical Modifications of the Subtilisins with Special Reference to the Binding of Large Substrates. A Review, >> Carlsberg Res. Comm., vol. 41, No. 5, pp. 237–291, 1976.

Tomkinson, Birgitta et al., << Characterization of cDNA for Human Tripeptidy Peptidase II : The N–Terminal Part of the Enzyme is Similar to Subtilisin, >> Biochem., vol. 30, pp. 168–174, 1991.

Wright, Christine et al., << Structure of Subtilisin BPN+ at 2 5 Å Resolution, >> Nature, vol. 221, pp. 235–242, 1969.

Barr et al, "cDNA and gene structure for a human subtilisin—like protease with cleavage for paired basic amino acid residues," DNA and Cell Biology, (Jun. 1991) 10 (5) pp. 319–328.

Kiefer et al., "Identification of a second human subtilisin—like gene in the fes/fps region of chromosomes 15," DNA and Cell biology, (Dec. 1991) 10 (10) pp. 757–769.

Padlan, E. A., "A possible Procedure for Reducing the Immunogenicity of Antibody variable domains while preserving their ligand–binding properties," Molecular Immunology, V. 28, No. 4/05, Apr. 1, 1991, pp. 489–498.

Ramnarayan et al., "Antibody humanization predicted by computer graphic anaylsis," American Biotechnology Laboratory, (Aug. 1995) 13 (9) 26, 28, whole document.

Siezen et al, "Homology modelling and protein engineering strategy of subtilases, the family of subtilisin–like serine proteinases," Protein Engineering, vol. 4, No. 7, Jan. 1, 1991, pp. 719–737.

* cited by examiner

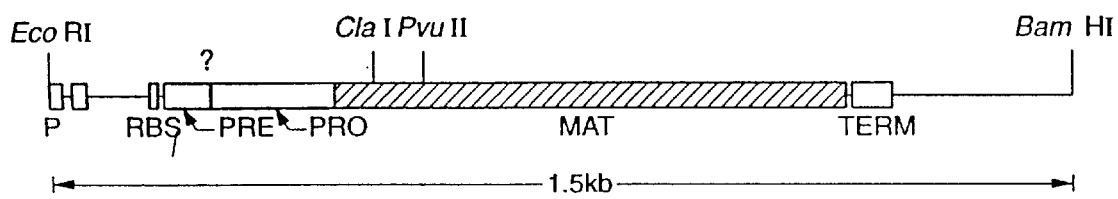
FIG._1A

```
           Gln Val Arg Ser Ser Leu Glu Asn Thr Thr Thr Lys Leu Gly Asp Ser Phe Tyr Tyr Gly Lys Gly Leu Ile Asn
                                250                                         260
1149       CAA GTC CGC AGC AGT TTA GAA AAC ACC ACT ACA AAA CTT GGT GAT TCT TTC TAC TAT GGA AAA GGG CTG ATC AAC

Val Gln Ala Ala Ala Gln                                          TERM
           270                 275
1224       GTA CAG GCG GCA GCT CAG TAA AACATAAAAACCGGGCCTTGGCCCCCCGGTTTTTATTTTCTTCCTCCGCATGTCAATCCGCTCC

1316       ATAATCGACGGATGGCTCCCTCTGAAAATTTTAACGAGAAACGGGCGGTTGACCCGGCTCAGTCCCGTAACGGCCAAGTCCTGAAACGTCTCAATCGCCG

1416       CTTCCCGGTTTCCGGTCAGCTCAATGCCGTAACGGTCGGGCGGTTTCCTGATACGGGAGACGGCATTCGTAATCGATC
```

*FIG._1B - 3*

| FIG._1B - 1 |
| FIG._1B - 2 |
| FIG._1B - 3 |

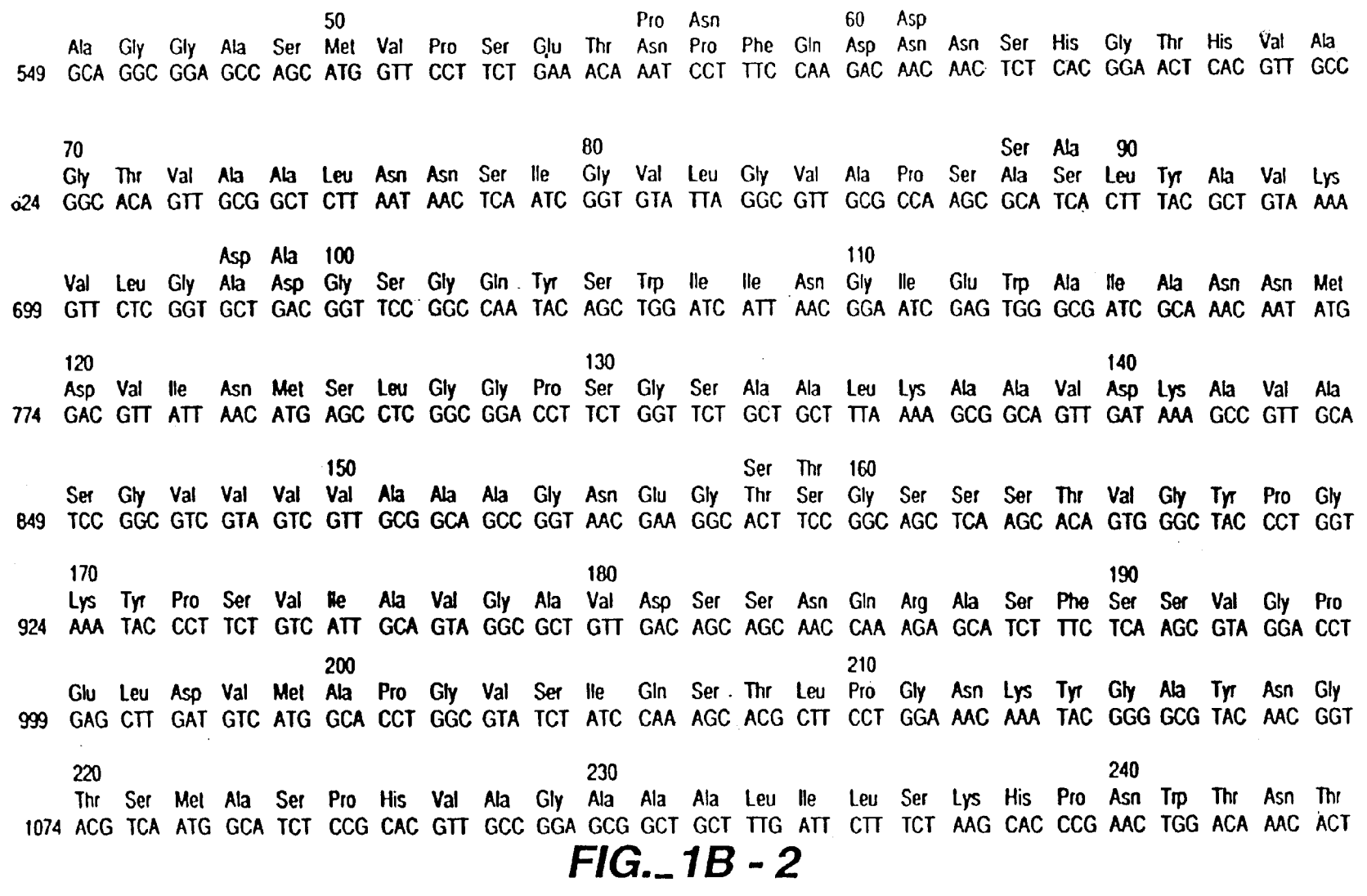

CONSERVED RESIDUES IN SUBTILISINS FROM
*BACILLUS AMYLOLIQUEFACIENS*

| FIG.–3A | FIG.–3B |

COMPARISON OF SUBTILISIN SEQUENCES FROM:
B.amyloliquefaciens
B.subtilis
B.licheniformis
B.lentus

MKLVNIWLLLLVVLLCGKKHLGDRLEKKSFEKAPCPGCSHLTLKVEFSSTVVEYEYIVAFNGYFT
AKARNSFISSALKSSEVDNWRIIPRNNPSSDYPSDFEVIQIKEKQKAGLLTLEDHPNIKRVTPQR
KVFRSLKYAESDPTVPCNETRWSQKWQSSRPLRRASLSLGSGFWHATGRHSSRRLLRAIPRQVAQ
TLQADVLWQMGYTGANVRVAVFDTGLSEKHPHFKNVKERTNWTNERTLDDGLGHGTFVAGVIASM
RECQGFAPDAELHIFRVFTNNQVSYTSWFLDAFNYAILKKIDVLNLSIGGPDFMDHPFVDKVWEL
TANNVIMVSAIGNDGPLYGTLNNPADQMDVIGVGGIDFEDNIARFSSRGMTTWELPGGYGRMKPD
IVTYGAGVRGSGVKGGCRALSGTSVASPVVAGAVTLLVSTVQKRELVNPASMKQALIASARRLPG
VNMFEQGHGKLDLLRAYQILNSYKPQASLSPSYIDLTECPYMWPYCSQPIYYGGMPTVVNVTILN
GMGVTGRIVDKPDWQPYLPQNGDNIEVAFSYSSVLWPWSGYLAISISVTKKAASWEGIAQGHVMI
TVASPAETESKNGAEQTSTVKLPIKVKIIPTPPRSKRVLWDQYHNLRYPPGYFPRDNLRMKNDPL
DWNGDHIHTNFRDMYQHLRSMGYFVEVLGAPFTCFDASQYGTLLMVDSEEEYFPEEIAKLRRDVD
NGLSLVIFSDWYNTSVMRKVKFYDENTRQWWMPDTGGANIPALNELLSVWNMGFSDGLYEGEFTL
ANHDMYYASGCSIAKFPEDGVVITQTFKDQGLEVLKQETAVVENVPILGLYQIPAEGGGRIVLYG
DSNCLDDSHRQKDCFWLLDALLQYTSYGVTPPSLSHSGNRQRPPSGAGSVTPERMEGNHLHRYSK
VLEAHLGDPKPRPLPACPRLSWAKPQPLNETAPSNLWKHQKLLSIDLDKVVLPNFRSNRPQVRPL
SPGESGAWDIPGGIMPGRYNQEVGQTIPVFAFLGAMVVLAFFVVQINKAKSRPKRRKPRVKRPQL
MQQVHPPKTPSV

FIG. 6

| | | | |
|---|---|---|---|
| Residues 135 – 149 of SEQ ID NO:3 | 2 | A11 | LEQAVNSATSRGVLV |
| Residues 1 – 15 of SEQ ID NO:3 | 3 | A10 | AQSVPWGISRVQAPA |
| Residues 4 – 18 of SEQ ID NO:3 | 4 | A9 | VPWGISRVQAPAAHN |
| Residues 7 – 21 of SEQ ID NO:3 | 5 | A8 | GISRVQAPAAHNRGL |
| Residues 10 – 24 of SEQ ID NO:3 | 6 | A7 | RVQAPAAHNRGLTGS |
| Residues 13 – 27 of SEQ ID NO:3 | 7 | A6 | APAAHNRGLTGSGVK |
| Residues 16 – 30 of SEQ ID NO:3 | 8 | A5 | AHNRGLTGSGVKVAV |
| Residues 19 – 33 of SEQ ID NO:3 | 9 | A4 | RGLTGSGVKVAVLDT |
| Residues 22 – 36 of SEQ ID NO:3 | 10 | A3 | TGSGVKVAVLDTGIS |
| Residues 25 – 39 of SEQ ID NO:3 | 11 | A2 | GVKVAVLDTGISTHP |
| Residues 28 – 42 of SEQ ID NO:3 | 12 | A1 | VAVLDTGISTHPDLN |
| Residues 31 – 45 of SEQ ID NO:3 | 13 | B12 | LDTGISTHPDLNIRG |
| Residues 34 – 48 of SEQ ID NO:3 | 14 | B11 | GISTHPDLNIRGGAS |
| Residues 37 – 51 of SEQ ID NO:3 | 15 | B10 | THPDLNIRGGASFVP |
| Residues 40 – 54 of SEQ ID NO:3 | 16 | B9 | DLNIRGGASFVPGEP |
| Residues 43 – 57 of SEQ ID NO:3 | 17 | B8 | IRGGASFVPGEPSTQ |
| Residues 46 – 60 of SEQ ID NO:3 | 18 | B7 | GASFVPGEPSTQDGN |
| Residues 49 – 63 of SEQ ID NO:3 | 19 | B6 | FVPGEPSTQDGNGHG |
| Residues 52 – 66 of SEQ ID NO:3 | 20 | B5 | GEPSTQDGNGHGTHV |
| Residues 55 – 69 of SEQ ID NO:3 | 21 | B4 | STQDGNGHGTHVAGT |
| Residues 58 – 72 of SEQ ID NO:3 | 22 | B3 | DGNGHGTHVAGTIAA |
| Residues 61 – 75 of SEQ ID NO:3 | 23 | B2 | GHGTHVAGTIAALNN |
| Residues 64 – 78 of SEQ ID NO:3 | 24 | B1 | THVAGTIAALNNSIG |
| Residues 67 – 81 of SEQ ID NO:3 | 25 | C12 | AGTIAALNNSIGVLG |
| Residues 70 – 84 of SEQ ID NO:3 | 26 | C11 | IAALNNSIGVLGVAP |
| Residues 73 – 87 of SEQ ID NO:3 | 27 | C10 | LNNSIGVLGVAPSAE |
| Residues 76 – 90 of SEQ ID NO:3 | 28 | C9 | SIGVLGVAPSAELYA |
| Residues 79 – 93 of SEQ ID NO:3 | 29 | C8 | VLGVAPSAELYAVKV |
| Residues 82 – 96 of SEQ ID NO:3 | 30 | C7 | VAPSAELYAVKVLGA |
| Residues 85 – 99 of SEQ ID NO:3 | 31 | C6 | SAELYAVKVLGASGS |
| Residues 88 – 102 of SEQ ID NO:3 | 32 | C5 | LYAVKVLGASGSGSV |
| Residues 91 – 105 of SEQ ID NO:3 | 33 | C4 | VKVLGASGSGSVSSI |
| Residues 94 – 108 of SEQ ID NO:3 | 34 | C3 | LGASGSGSVSSIAQG |
| Residues 97 – 111 of SEQ ID NO:3 | 35 | C2 | SGSGSVSSIAQGLEW |
| Residues 100 – 114 of SEQ ID NO:3 | 36 | C1 | GSVSSIAQGLEWAGN |
| Residues 103 – 117 of SEQ ID NO:3 | 37 | D12 | SSIAQGLEWAGNNGM |
| Residues 106 – 120 of SEQ ID NO:3 | 38 | D11 | AQGLEWAGNNGMHVA |
| Residues 109 – 123 of SEQ ID NO:3 | 39 | D10 | LEWAGNNGMHVANLS |
| Residues 112 – 126 of SEQ ID NO:3 | 40 | D9 | AGNNGMHVANLSLGS |
| Residues 115 – 129 of SEQ ID NO:3 | 41 | D8 | NGMHVANLSLGSPSP |

FIG. 7A

| | | | |
|---|---|---|---|
| Residues 118 – 132 of SEQ ID NO:3 | 42 | D7 | HVANLSLGSPSPSAT |
| Residues 121 – 135 of SEQ ID NO:3 | 43 | D6 | NLSLGSPSPSATLEQ |
| Residues 124 –138 of SEQ ID NO:3 | 44 | D5 | LGSPSPSATLEQAVN |
| Residues 127 – 141 of SEQ ID NO:3 | 45 | D4 | PSPSATLEQAVNSAT |
| Residues 130 – 144 of SEQ ID NO:3 | 46 | D3 | SATLEQAVNSATSRG |
| Residues 133 – 147 of SEQ ID NO:3 | 47 | D2 | LEQAVNSATSRGVLV |
| Residues 136 – 150 of SEQ ID NO:3 | 48 | D1 | AVNSATSRGVLVVAA |
| Residues 139 – 153 of SEQ ID NO:3 | 49 | E12 | SATSRGVLVVAASGN |
| Residues 142 – 156 of SEQ ID NO:3 | 50 | E11 | SRGVLVVAASGNSGA |
| Residues 145 – 159 of SEQ ID NO:3 | 51 | E10 | VLVVAASGNSGAGSI |
| Residues 148 – 162 of SEQ ID NO:3 | 52 | E9 | VAASGNSGAGSISYP |
| Residues 151 – 165 of SEQ ID NO:3 | 53 | E8 | SGNSGAGSISYPARY |
| Residues 154 – 168 of SEQ ID NO:3 | 54 | E7 | SGAGSISYPARYANA |
| Residues 157 – 171 of SEQ ID NO:3 | 55 | E6 | GSISYPARYANAMAV |
| Residues 160 – 174 of SEQ ID NO:3 | 56 | E5 | SYPARYANAMAVGAT |
| Residues 163 – 177 of SEQ ID NO:3 | 57 | E4 | ARYANAMAVGATDQN |
| Residues 166 – 180 of SEQ ID NO:3 | 58 | E3 | ANAMAVGATDQNNNR |
| Residues 169 – 183 of SEQ ID NO:3 | 59 | E2 | MAVGATDQNNNRASF |
| Residues 172 – 186 of SEQ ID NO:3 | 60 | E1 | GATDQNNNRASFSQY |
| Residues 175 – 189 of SEQ ID NO:3 | 61 | F12 | DQNNNRASFSQYGAG |
| Residues 178 – 192 of SEQ ID NO:3 | 62 | F11 | NNRASFSQYGAGLDI |
| Residues 181 – 195 of SEQ ID NO:3 | 63 | F10 | ASFSQYGAGLDIVAP |
| Residues 184 – 198 of SEQ ID NO:3 | 64 | F9 | SQYGAGLDIVAPGVN |
| Residues 187 – 201 of SEQ ID NO:3 | 65 | F8 | GAGLDIVAPGVNVQS |
| Residues 190 – 204 of SEQ ID NO:3 | 66 | F7 | LDIVAPGVNVQSTYP |
| Residues 193 – 207 of SEQ ID NO:3 | 67 | F6 | VAPGVNVQSTYPGST |
| Residues 196 – 210 of SEQ ID NO:3 | 68 | F5 | GVNVQSTYPGSTYAS |
| Residues 199 – 213 of SEQ ID NO:3 | 69 | F4 | VQSTYPGSTYASLNG |
| Residues 202 – 216 of SEQ ID NO:3 | 70 | F3 | TYPGSTYASLNGTSM |
| Residues 205 – 219 of SEQ ID NO:3 | 71 | F2 | GSTYASLNGTSMATP |
| Residues 208 – 222 of SEQ ID NO:3 | 72 | F1 | YASLNGTSMATPHVA |
| Residues 211 – 225 of SEQ ID NO:3 | 73 | G12 | LNGTSMATPHVAGAA |
| Residues 214 – 228 of SEQ ID NO:3 | 74 | G11 | TSMATPHVAGAAALV |
| Residues 217 – 231 of SEQ ID NO:3 | 75 | G10 | ATPHVAGAAALVKQK |
| Residues 220 – 234 of SEQ ID NO:3 | 76 | G9 | HVAGAAALVKQKNPS |
| Residues 223 – 237 of SEQ ID NO:3 | 77 | G8 | GAAALVKQKNPSWSN |
| Residues 226 – 240 of SEQ ID NO:3 | 78 | G7 | ALVKQKNPSWSNVQI |
| Residues 229 – 243 of SEQ ID NO:3 | 79 | G6 | KQKNPSWSNVQIRNH |
| Residues 232 – 246 of SEQ ID NO:3 | 80 | G5 | NPSWSNVQIRNHLKN |
| Residues 235 – 249 of SEQ ID NO:3 | 81 | G4 | WSNVQIRNHLKNTAT |
| Residues 238 – 252 of SEQ ID NO:3 | 82 | G3 | VQIRNHLKNTATSLG |

FIG. 7B

| | | | |
|---|---|---|---|
| Residues 241 – 255 of SEQ ID NO:3 | 83 | G2 | RNHLKNTATSLGSTN |
| Residues 244 – 258 of SEQ ID NO:3 | 84 | G1 | LKNTATSLGSTNLYG |
| Residues 247 – 261 of SEQ ID NO:3 | 85 | H12 | TATSLGSTNLYGSGL |
| Residues 250 – 264 of SEQ ID NO:3 | 86 | H11 | SLGSTNLYGSGLVNA |
| Residues 253 – 267 of SEQ ID NO:3 | 87 | H10 | STNLYGSGLVNAEAA |
| Residues 256 – 270 of SEQ ID NO:3 | 88 | H9 | NLYGSGLVNAEAATR |

FIG. 7C

| | | | |
|---|---|---|---|
| Residues 269 – 283 of SEQ ID NO:6 | 2 | A11 | DAELHIFRVFTNNQV |
| Residues 161 – 175 of SEQ ID NO:6 | 3 | A10 | PLRRASLSLGSGFWH |
| Residues 164 – 178 of SEQ ID NO:6 | 4 | A9 | RASLSLGSFWHATG |
| Residues 167 - 181 of SEQ ID NO:6 | 5 | A8 | LSLGSGFWHATGRHS |
| Residues 170 – 184 of SEQ ID NO:6 | 6 | A7 | GSGFWHATGRHSSRR |
| Residues 173 – 187 of SEQ ID NO:6 | 7 | A6 | FWHATGRHSSRRLLR |
| Residues 176 – 190 of SEQ ID NO:6 | 8 | A5 | ATGRHSSRRLLRAIP |
| Residues 179 – 193 of SEQ ID NO:6 | 9 | A4 | RHSSRRLLRAIPRQV |
| Residues 182 – 196 of SEQ ID NO:6 | 10 | A3 | SRRLLRAIPRQVAQT |
| Residues 185 – 199 of SEQ ID NO:6 | 11 | A2 | LLRAIPRQVAQTLQA |
| Residues 188 – 202 of SEQ ID NO:6 | 12 | A1 | AIPRQVAQTLQADVL |
| Residues 191 – 205 of SEQ ID NO:6 | 13 | B12 | RQVAQTLQADVLWQM |
| Residues 194 – 208 of SEQ ID NO:6 | 14 | B11 | AQTLQADVLWQMGYT |
| Residues 197 – 211 of SEQ ID NO:6 | 15 | B10 | LQADVLWQMGYTGAN |
| Residues 200 - 214 of SEQ ID NO:6 | 16 | B9 | DVLWQMGYTGANVRV |
| Residues 203 – 217 of SEQ ID NO:6 | 17 | B8 | WQMGYTGANVRVAVF |
| Residues 206 – 220 of SEQ ID NO:6 | 18 | B7 | GYTGANVRVAVFDTG |
| Residues 209 – 223 of SEQ ID NO:6 | 19 | B6 | GANVRVAVFDTGLSE |
| Residues 212 – 226 of SEQ ID NO:6 | 20 | B5 | VRVAVFDTGLSEKHP |
| Residues 215 – 229 of SEQ ID NO:6 | 21 | B4 | AVFDTGLSEKHPHFK |
| Residues 218 – 232 of SEQ ID NO:6 | 22 | B3 | DTGLSEKHPHFKNVK |
| Residues 221 – 235 of SEQ ID NO:6 | 23 | B2 | LSEKHPHFKNVKERT |
| Residues 224 – 238 of SEQ ID NO:6 | 24 | B1 | KHPHFKNVKERTNWT |
| Residues 227 – 241 of SEQ ID NO:6 | 25 | C12 | HFKNVKERTNWTNER |
| Residues 230 – 244 of SEQ ID NO:6 | 26 | C11 | NVKERTNWTNERTLD |
| Residues 233 – 247 of SEQ ID NO:6 | 27 | C10 | ERTNWTNERTLDDGL |
| Residues 236 – 250 of SEQ ID NO:6 | 28 | C9 | NWTNERTLDDGLGHG |
| Residues 239 – 253 of SEQ ID NO:6 | 29 | C8 | NERTLDDGLGHGTFV |
| Residues 242 – 256 of SEQ ID NO:6 | 30 | C7 | TLDDGLGHGTFVAGV |
| Residues 245 – 259 of SEQ ID NO:6 | 31 | C6 | DGLGHGTFVAGVIAS |
| Residues 248 – 262 of SEQ ID NO:6 | 32 | C5 | GHGTFVAGVIASMRE |
| Residues 251 – 265 of SEQ ID NO:6 | 33 | C4 | TFVAGVIASMRECQG |
| Residues 254 – 268 of SEQ ID NO:6 | 34 | C3 | AGVIASMRECQGFAP |
| Residues 257 – 271 of SEQ ID NO:6 | 35 | C2 | IASMRECQGFAPDAE |
| Residues 260 – 274 of SEQ ID NO:6 | 36 | C1 | MRECQGFAPDAELHI |
| Residues 263 – 277 of SEQ ID NO:6 | 37 | D12 | CQGFAPDAELHIFRV |
| Residues 266 – 280 of SEQ ID NO:6 | 38 | D11 | FAPDAELHIFRVFTN |
| Residues 269 – 283 of SEQ ID NO:6 | 39 | D10 | DAELHIFRVFTNNOV |

FIG. 8A

| | | | |
|---|---|---|---|
| Residues 272 – 286 of SEQ ID NO:6 | 40 | D9 | LHIFRVFTNNQVSYT |
| Residues 275 – 289 of SEQ ID NO:6 | 41 | D8 | FRVFTNNQVSYTSWF |
| Residues 278 – 292 of SEQ ID NO:6 | 42 | D7 | FTNNQVSYTSWFLDA |
| Residues 281 – 295 of SEQ ID NO:6 | 43 | D6 | NQVSYTSWFLDAFNY |
| Residues 284 – 298 of SEQ ID NO:6 | 44 | D5 | SYTSWFLDAFNYAIL |
| Residues 287 – 301 of SEQ ID NO:6 | 45 | D4 | SWFLDAFNYAILKKI |
| Residues 290 – 304 of SEQ ID NO:6 | 46 | D3 | LDAFNYAILKKIDVL |
| Residues 293 – 307 of SEQ ID NO:6 | 47 | D2 | FNYAILKKIDVLNLS |
| Residues 296 – 310 of SEQ ID NO:6 | 48 | D1 | AILKKIDVLNLSIGG |
| Residues 299 – 313 of SEQ ID NO:6 | 49 | E12 | KKIDVLNLSIGGPDF |
| Residues 302 – 316 of SEQ ID NO:6 | 50 | E11 | DVLNLSIGGPDFMDH |
| Residues 305 – 319 of SEQ ID NO:6 | 51 | E10 | NLSIGGPDFMDHPFV |
| Residues 308 – 322 of SEQ ID NO:6 | 52 | E9 | IGGPDFMDHPFVDKV |
| Residues 311 – 325 of SEQ ID NO:6 | 53 | E8 | PDFMDHPFVDKVWEL |
| Residues 314 – 328 of SEQ ID NO:6 | 54 | E7 | MDHPFVDKVWELTAN |
| Residues 317 – 331 of SEQ ID NO:6 | 55 | E6 | PFVDKVWELTANNVI |
| Residues 320 – 334 of SEQ ID NO:6 | 56 | E5 | DKVWELTANNVIMVS |
| Residues 323 – 337 of SEQ ID NO:6 | 57 | E4 | WELTANNVIMVSAIG |
| Residues 326 – 340 of SEQ ID NO:6 | 58 | E3 | TANNVIMVSAIGNDG |
| Residues 329 – 343 of SEQ ID NO:6 | 59 | E2 | NVIMVSAIGNDGPLY |
| Residues 332 – 346 of SEQ ID NO:6 | 60 | E1 | MVSAIGNDGPLYGTJ |
| Residues 335 – 349 of SEQ ID NO:6 | 61 | F12 | AIGNDGPLYGTLNNP |
| Residues 338 – 352 of SEQ ID NO:6 | 62 | F11 | NDGPLYGTLNNPADQ |
| Residues 341 – 355 of SEQ ID NO:6 | 63 | F10 | PLYGTLNNPADQMDV |
| Residues 344 – 358 of SEQ ID NO:6 | 64 | F9 | GTLNNPADQMDVIGV |
| Residues 347 – 361 of SEQ ID NO:6 | 65 | F8 | NNPADQMDVIGVGGI |
| Residues 350 – 364 of SEQ ID NO:6 | 66 | F7 | ADQMDVIGVGGIDFE |
| Residues 353 – 367 of SEQ ID NO:6 | 67 | F6 | MDVIGVGGIDFEDNI |
| Residues 356 – 370 of SEQ ID NO:6 | 68 | F5 | IGVGGIDFEDNIARF |
| Residues 359 – 373 of SEQ ID NO:6 | 69 | F4 | GGIDFEDNIARFSSR |
| Residues 362 – 376 of SEQ ID NO:6 | 70 | F3 | DFEDNIARFSSRGMT |
| Residues 365 – 379 of SEQ ID NO:6 | 71 | F2 | DNIARFSSRGMTTWE |
| Residues 368 – 382 of SEQ ID NO:6 | 72 | F1 | ARFSSRGMTTWELPG |
| Residues 371 – 385 of SEQ ID NO:6 | 73 | G12 | SSRGMTTWELPGGYG |
| Residues 374 – 388 of SEQ ID NO:6 | 74 | G11 | GMTTWELPGGYGRMK |
| Residues 377 – 391 of SEQ ID NO:6 | 75 | G10 | TWELPGGYGRMKPDI |
| Residues 380 – 394 of SEQ ID NO:6 | 76 | G9 | LPGGYGRMKPDIVTY |
| Residues 383 – 397 of SEQ ID NO:6 | 77 | G8 | GYGRMKPDIVTYGAG |
| Residues 386 – 400 of SEQ ID NO:6 | 78 | G7 | RMKPDIVTYGAGVRG |
| Residues 389 – 403 of SEQ ID NO:6 | 79 | G6 | PDIVTYGAGVRGSGV |

FIG. 8B

| | | | |
|---|---|---|---|
| Residues 392 – 406 of SEQ ID NO:6 | 80 | G5 | VTYGAGVRGSGVKGG |
| Residues 395 – 409 of SEQ ID NO:6 | 81 | G4 | GAGVRGSGVKGGCRA |
| Residues 398 – 412 of SEQ ID NO:6 | 82 | G3 | VRGSGVKGGCRALSG |
| Residues 401 – 415 of SEQ ID NO:6 | 83 | G2 | SGVKGGCRALSGTSV |
| Residues 404 – 418 of SEQ ID NO:6 | 84 | G1 | KGGCRALSGTSVASP |
| Residues 407 – 421 of SEQ ID NO:6 | 85 | H12 | CRALSGTSVASPVVA |
| Residues 410 – 424 of SEQ ID NO:6 | 86 | H11 | LSGTSVASPVVAGAV |
| Residues 413 – 427 of SEQ ID NO:6 | 87 | H10 | TSVASPVVAGAVTLL |
| Residues 416 – 430 of SEQ ID NO:6 | 88 | H9 | ASPVVAGAVTLLVST |
| Residues 419 – 433 of SEQ ID NO:6 | 89 | H8 | VVAGAVTLLVSTVQK |
| Residues 422 – 436 of SEQ ID NO:6 | 90 | H7 | GAVTLLVSTVQKREL |
| Residues 425 – 439 of SEQ ID NO:6 | 91 | H6 | YLLVSTVQKRELVNP |
| Residues 428 – 442 of SEQ ID NO:6 | 92 | H5 | VSTVQKRELVNPASM |
| Residues 431 – 445 of SEQ ID NO:6 | 93 | H4 | VQKRELVNPASMKQA |
| Residues 434 – 448 of SEQ ID NO:6 | 94 | H3 | RELVNPASMKQALIA |
| Residues 437 – 451 of SEQ ID NO:6 | 95 | H2 | VNPASMKQALIASAR |
| Residues 440 – 455 of SEQ ID NO:6 | 96 | H1 | ASMKQALIASARRLP |
| Residues 269 – 283 of SEQ ID NO:6 | 98 | I11 | DAELHIFRVFTNNQV |
| Residues 443 – 457 of SEQ ID NO:6 | 99 | I10 | KQALIASARRLPGVN |
| Residues 446 – 460 of SEQ ID NO:6 | 100 | I9 | LIASARRLPGVNMFE |
| Residues 449 – 463 of SEQ ID NO:6 | 101 | I8 | SARRLPGNNMFEQGH |
| Residues 452 – 466 of SEQ ID NO:6 | 102 | I7 | RLPGVNMFEQGHGKL |
| Residues 455 – 469 of SEQ ID NO:6 | 103 | I6 | GVNMFEQGHGKLDLL |
| Residues 458 – 472 of SEQ ID NO:6 | 104 | I5 | MFEQGHGKLDLLRAY |
| Residues 461 – 475 of SEQ ID NO:6 | 105 | I4 | QGHGKLDLLRAYQIL |
| Residues 464 – 478 of SEQ ID NO:6 | 106 | I3 | GKLDLLRAYQILNSY |
| Residues 467 – 481 of SEQ ID NO:6 | 107 | I2 | DLLRAYQILNSYKPQ |
| Residues 470 – 484 of SEQ ID NO:6 | 108 | I1 | RAYQILNSYKPQASL |
| Residues 473 – 487 of SEQ ID NO:6 | 109 | J12 | QILNSYKPQASLAPS |
| Residues 476 – 490 of SEQ ID NO:6 | 110 | J11 | NSYKPQASLSPSYID |
| Residues 479 – 493 of SEQ ID NO:6 | 111 | J10 | KPQASLSPSYIDLTE |
| Residues 482 – 496 of SEQ ID NO:6 | 112 | J9 | ASLSPSYIDLTECPY |
| Residues 485 – 499 of SEQ ID NO:6 | 113 | J8 | SPSYIDLTECPYMWP |
| Residues 488 – 502 of SEQ ID NO:6 | 114 | J7 | YIDLTECPYMWPYCS |
| Residues 491 – 505 of SEQ ID NO:6 | 115 | J6 | LTECPYMWPYCSQPI |
| Residues 494 – 508 of SEQ ID NO:6 | 116 | J5 | CPYMWPYCSQPIYYG |

FIG. 8C

SEQUENCE LISTING

<160> NUMBER OF SEQ ID NOS: 7

<210> SEQ ID NO 1
<211> LENGTH: 1497
<212> TYPE: DNA
<213> ORGANISM: B. amyloliquefaciens
<220> FEATURE:
<221> NAME/KEY: CDS
<222> LOCATION: (96)...(1245)

<400> SEQUENCE: 1

```
ggtctactaa aatattattc catactatac aattaataca cagaataatc tgtctattgg       60
ttattctgca aatgaaaaaa aggagaggat aaaga gtg aga ggc aaa aaa gta         113
                                       Val Arg Gly Lys Lys Val
                                         1               5 tgg atc agt ttg ctg ttt gct tta gcg tta atc ttt acg atg gcg ttc        161
Trp Ile Ser Leu Leu Phe Ala Leu Ala Leu Ile Phe Thr Met Ala Phe
             10                  15                  20 ggc agc aca tcc tct gcc cag gcg gca ggg aaa tca aac ggg gaa aag        209
Gly Ser Thr Ser Ser Ala Gln Ala Ala Gly Lys Ser Asn Gly Glu Lys
         25                  30                  35 aa tat att gtc ggg ttt aaa cag aca atg agc acg atg agc gcc gct        257
Lys Tyr Ile Val Gly Phe Lys Gln Thr Met Ser Thr Met Ser Ala Ala
   40                  45                  50 aag aag aaa gat gtc att tct gaa aaa ggc ggg aaa gtg caa aag caa       305
Lys Lys Lys Asp Val Ile Ser Glu Lys Gly Gly Lys Val Gln Lys Gln
 55                  60                  65                  70 ttc aaa tat gta gac gca gct tca gtc aca tta aac gaa aaa gct gta       353
Phe Lys Tyr Val Asp Ala Ala Ser Val Thr Leu Asn Glu Lys Ala Val
                 75                  80                  85 aaa gaa ttg aaa aaa gac ccg agc gtc gct tac gtt gaa gaa gat cac       401
Lys Glu Leu Lys Lys Asp Pro Ser Val Ala Tyr Val Glu Glu Asp His
             90                  95                 100 ta gca cat gcg tac gcg cag tcc gtg cct tac ggc gta tca caa att       449
Val Ala His Ala Tyr Ala Gln Ser Val Pro Tyr Gly Val Ser Gln Ile
       105                 110                 115 aaa gcc cct gct ctg cac tct caa ggc tac act gga tca aat gtt aaa       497
Lys Ala Pro Ala Leu His Ser Gln Gly Tyr Thr Gly Ser Asn Val Lys
   120                 125                 130 gta gcg gtt atc gac agc ggt atc gat tct tct cat cct gat tta aag       545
Val Ala Val Ile Asp Ser Gly Ile Asp Ser Ser His Pro Asp Leu Lys
135                 140                 145                 150 gta gca agc gga gcc agc atg gtt cct tct gaa aca aat cct ttc caa       593
Val Ala Ser Gly Ala Ser Met Val Pro Ser Glu Thr Asn Pro Phe Gln
                155                 160                 165 gac aac aac tct cac gga act cac gtt gcc ggc aca gtt gcg gct ctt       641
Asp Asn Asn Ser His Gly Thr His Val Ala Gly Thr Val Ala Ala Leu
            170                 175                 180 aat aac tca atc ggt gta tta ggc gtt gcg cca agc gca tca ctt tac       689
Asn Asn Ser Ile Gly Val Leu Gly Val Ala Pro Ser Ala Ser Leu Tyr
        185                 190                 195 gct gta aaa gtt ctc ggt gct gac ggt tcc ggc caa tac agc tgg atc       737
Ala Val Lys Val Leu Gly Ala Asp Gly Ser Gly Gln Tyr Ser Trp Ile
    200                 205                 210 att aac gga atc gag tgg gcg atc gca aac aat atg gac gtt att aac       785
Ile Asn Gly Ile Glu Trp Ala Ile Ala Asn Asn Met Asp Val Ile Asn
215                 220                 225                 230 tg agc ctc ggc gga cct tct ggt tct gct gct tta aaa gcg gca gtt       833
Met Ser Leu Gly Gly Pro Ser Gly Ser Ala Ala Leu Lys Ala Ala Val
```

```
gat aaa gcc gtt gca tcc ggc gtc gta gtc gtt gcg gca gcc ggt aac    881
Asp Lys Ala Val Ala Ser Gly Val Val Val Val Ala Ala Ala Gly Asn
        250                 255                 260 gaa ggc act tcc ggc agc tca agc aca gtg ggc tac cct ggt aaa tac    929
Glu Gly Thr Ser Gly Ser Ser Ser Thr Val Gly Tyr Pro Gly Lys Tyr
        265                 270                 275 cct tct gtc att gca gta ggc gct gtt gac agc agc aac caa aga gca    977
Pro Ser Val Ile Ala Val Gly Ala Val Asp Ser Ser Asn Gln Arg Ala
        280                 285                 290 tct ttc tca agc gta gga cct gag ctt gat gtc atg gca cct ggc gta   1025
Ser Phe Ser Ser Val Gly Pro Glu Leu Asp Val Met Ala Pro Gly Val
295                 300                 305                 310 tct atc caa agc acg ctt cct gga aac aaa tac ggg gcg tac aac ggt   1073
Ser Ile Gln Ser Thr Leu Pro Gly Asn Lys Tyr Gly Ala Tyr Asn Gly
        315                 320                 325 acg tca atg gca tct ccg cac gtt gcc gga gcg gct gct ttg att ctt   1121
Thr Ser Met Ala Ser Pro His Val Ala Gly Ala Ala Ala Leu Ile Leu
        330                 335                 340 ct aag cac ccg aac tgg aca aac act caa gtc cgc agc agt tta gaa    1169
Ser Lys His Pro Asn Trp Thr Asn Thr Gln Val Arg Ser Ser Leu Glu
        345                 350                 355 aac acc act aca aaa ctt ggt gat tct ttg tac tat gga aaa ggg ctg   1217
Asn Thr Thr Lys Leu Gly Asp Ser Leu Tyr Tyr Gly Lys Gly Leu
360                 365                 370 atc aac gta caa gcg gca gct cag taa a acataaaaaa ccggccttgg       1265
Ile Asn Val Gln Ala Ala Ala Gln  *
375                 380 ccccgccggt ttttttattat ttttcttcct ccgcatgttc aatccgctcc ataatcgacg  1325
gatggctccc tctgaaaatt ttaacgagaa acggcgggtt gacccggctc agtcccgtaa   1385
cggccaactc ctgaaacgtc tcaatcgccg cttcccggtt tccggtcagc tcaatgccat   1445
aacggtcggc ggcgttttcc tgataccggg agacggcatt cgtaatcgga tc          1497

<210> SEQ ID NO 2
<211> LENGTH: 1497
<212> TYPE: PRT
<213> ORGANISM: B. amyloliquefaciens

<400> SEQUENCE: 2

Gly Gly Thr Cys Thr Ala Cys Thr Ala Ala Ala Thr Ala Thr Thr
1               5                   10                  15

Ala Thr Thr Cys Cys Ala Thr Ala Cys Thr Ala Thr Cys Ala Ala
                20                  25                  30

Thr Thr Ala Ala Thr Ala Cys Ala Cys Ala Gly Ala Ala Thr Ala Ala
        35                  40                  45

Thr Cys Thr Gly Thr Cys Thr Ala Thr Thr Gly Thr Thr Ala Thr
    50                  55                  60

Thr Cys Thr Gly Cys Ala Ala Ala Thr Gly Ala Ala Ala Ala Ala
65                  70                  75                  80

Ala Gly Gly Ala Gly Ala Gly Gly Ala Thr Ala Ala Gly Ala Gly
                85                  90                  95

Thr Gly Ala Gly Ala Gly Gly Cys Ala Ala Ala Ala Ala Gly Thr
            100                 105                 110

Ala Thr Gly Gly Ala Thr Cys Ala Gly Thr Thr Gly Cys Thr Gly
            115                 120                 125

Thr Thr Thr Gly Cys Thr Thr Thr Ala Gly Cys Gly Thr Thr Ala Ala
```

-continued

```
            130                 135                 140
Thr Cys Thr Thr Thr Ala Cys Gly Ala Thr Gly Cys Gly Thr Thr
145                 150                 155                 160
Cys Gly Gly Cys Ala Gly Cys Ala Cys Ala Thr Cys Cys Thr Cys Thr
                165                 170                 175
Gly Cys Cys Cys Ala Gly Gly Cys Gly Gly Cys Ala Gly Gly Gly Ala
                180                 185                 190
Ala Ala Thr Cys Ala Ala Cys Gly Gly Gly Ala Ala Ala
            195                 200                 205
Gly Ala Ala Thr Ala Thr Ala Thr Gly Thr Cys Gly Gly Gly
210                 215                 220
Thr Thr Thr Ala Ala Ala Cys Ala Gly Ala Cys Ala Ala Thr Gly Ala
225                 230                 235                 240
Gly Cys Ala Cys Gly Ala Thr Gly Ala Gly Cys Gly Cys Cys Gly Cys
                245                 250                 255
Thr Ala Ala Gly Ala Ala Gly Ala Ala Ala Gly Ala Thr Gly Thr Cys
                260                 265                 270
Ala Thr Thr Thr Cys Thr Gly Ala Ala Ala Ala Gly Gly Cys Gly
            275                 280                 285
Gly Gly Ala Ala Ala Gly Thr Gly Cys Ala Ala Ala Gly Cys Ala
            290                 295                 300
Ala Thr Thr Cys Ala Ala Ala Thr Ala Thr Gly Thr Ala Gly Ala Cys
305                 310                 315                 320
Gly Cys Ala Gly Cys Thr Thr Cys Ala Gly Thr Cys Ala Cys Ala Thr
                325                 330                 335
Thr Ala Ala Ala Cys Gly Ala Ala Ala Ala Gly Cys Thr Gly Thr
            340                 345                 350
Ala Ala Ala Ala Gly Ala Ala Thr Thr Gly Ala Ala Ala Ala Ala
            355                 360                 365
Gly Ala Cys Cys Cys Gly Ala Gly Cys Gly Thr Cys Gly Cys Thr Thr
            370                 375                 380
Ala Cys Gly Thr Thr Gly Ala Ala Gly Ala Ala Gly Ala Thr Cys Ala
385                 390                 395                 400
Cys Gly Thr Ala Gly Cys Ala Cys Ala Thr Gly Cys Gly Thr Ala Cys
                405                 410                 415
Gly Cys Gly Cys Ala Gly Thr Cys Cys Gly Thr Gly Cys Cys Thr Thr
                420                 425                 430
Ala Cys Gly Gly Cys Gly Thr Ala Thr Cys Ala Cys Ala Ala Ala Thr
            435                 440                 445
Thr Ala Ala Ala Gly Cys Cys Cys Thr Gly Cys Thr Cys Thr Gly
            450                 455                 460
Cys Ala Cys Thr Cys Thr Cys Ala Ala Gly Gly Cys Thr Ala Cys Ala
465                 470                 475                 480
Cys Thr Gly Gly Ala Thr Cys Ala Ala Ala Thr Gly Thr Thr Ala Ala
                485                 490                 495
Ala Gly Thr Ala Gly Cys Gly Gly Thr Thr Ala Thr Cys Gly Ala Cys
            500                 505                 510
Ala Gly Cys Gly Gly Thr Ala Thr Cys Gly Ala Thr Thr Cys Thr Thr
            515                 520                 525
Cys Thr Cys Ala Thr Cys Cys Thr Gly Ala Thr Thr Ala Ala Ala
            530                 535                 540
Gly Gly Thr Ala Gly Cys Ala Ala Gly Cys Gly Gly Ala Gly Cys Cys
545                 550                 555                 560
```

-continued

Ala Gly Cys Ala Thr Gly Gly Thr Thr Cys Cys Thr Thr Cys Thr Gly
565 570 575

Ala Ala Ala Cys Ala Ala Ala Thr Cys Cys Thr Thr Thr Cys Cys Ala
580 585 590

Ala Gly Ala Cys Ala Ala Cys Ala Ala Cys Thr Cys Thr Cys Ala Cys
595 600 605

Gly Gly Ala Ala Cys Thr Cys Ala Cys Gly Thr Thr Gly Cys Cys Gly
610 615 620

Gly Cys Ala Cys Ala Gly Thr Thr Gly Cys Gly Gly Cys Thr Cys Thr
625 630 635 640

Thr Ala Ala Thr Ala Ala Cys Thr Cys Ala Ala Thr Cys Gly Gly Thr
645 650 655

Gly Thr Ala Thr Thr Ala Gly Gly Cys Gly Thr Thr Gly Cys Gly Cys
660 665 670

Cys Ala Ala Gly Cys Gly Cys Ala Thr Cys Ala Cys Thr Thr Thr Ala
675 680 685

Cys Gly Cys Thr Gly Thr Ala Ala Ala Ala Gly Thr Thr Cys Thr Cys
690 695 700

Gly Gly Thr Gly Cys Thr Gly Ala Cys Gly Gly Thr Thr Cys Cys Gly
705 710 715 720

Gly Cys Cys Ala Ala Thr Ala Cys Ala Gly Cys Thr Gly Gly Ala Thr
725 730 735

Cys Ala Thr Thr Ala Ala Cys Gly Gly Ala Ala Thr Cys Gly Ala Gly
740 745 750

Thr Gly Gly Gly Cys Gly Ala Thr Cys Gly Cys Ala Ala Ala Cys Ala
755 760 765

Ala Thr Ala Thr Gly Gly Ala Cys Gly Thr Thr Ala Thr Thr Ala Ala
770 775 780

Cys Ala Thr Gly Ala Gly Cys Cys Thr Cys Gly Gly Cys Gly Gly Ala
785 790 795 800

Cys Cys Thr Thr Cys Thr Gly Gly Thr Thr Cys Thr Gly Cys Thr Gly
805 810 815

Cys Thr Thr Thr Ala Ala Ala Ala Gly Cys Gly Gly Cys Ala Gly Thr
820 825 830

Thr Gly Ala Thr Ala Ala Ala Gly Cys Cys Gly Thr Thr Gly Cys Ala
835 840 845

Thr Cys Cys Gly Gly Cys Gly Thr Cys Gly Thr Ala Gly Thr Cys Gly
850 855 860

Thr Thr Gly Cys Gly Gly Cys Ala Gly Cys Cys Gly Gly Thr Ala Ala
865 870 875 880

Cys Gly Ala Ala Gly Gly Cys Ala Cys Thr Thr Cys Cys Gly Gly Cys
885 890 895

Ala Gly Cys Thr Cys Ala Ala Gly Cys Ala Cys Ala Gly Thr Gly Gly
900 905 910

Gly Cys Thr Ala Cys Cys Cys Thr Gly Gly Thr Ala Ala Ala Thr Ala
915 920 925

Cys Cys Cys Thr Thr Cys Thr Gly Thr Cys Ala Thr Thr Gly Cys Ala
930 935 940

Gly Thr Ala Gly Gly Cys Gly Cys Thr Gly Thr Thr Gly Ala Cys Ala
945 950 955 960

Gly Cys Ala Gly Cys Ala Ala Cys Cys Ala Ala Ala Gly Ala Gly Cys
965 970 975

-continued

Ala Thr Cys Thr Thr Thr Cys Thr Cys Ala Ala Gly Cys Gly Thr Ala
              980                 985                 990

Gly Gly Ala Cys Cys Thr Gly Ala Gly Cys Thr Thr Gly Ala Thr Gly
          995                1000                1005

Thr Cys Ala Thr Gly Gly Cys Ala Cys Thr Gly Gly Cys Gly Thr
      1010                1015                1020

Ala Thr Cys Thr Ala Thr Cys Cys Ala Ala Gly Cys Ala Cys Gly
1025                1030                1035                1040

Cys Thr Thr Cys Thr Gly Gly Ala Ala Cys Ala Ala Thr
              1045                1050                1055

Ala Cys Gly Gly Gly Gly Cys Gly Thr Ala Cys Ala Ala Cys Gly Gly
              1060                1065                1070

Thr Ala Cys Gly Thr Cys Ala Ala Thr Gly Gly Cys Ala Thr Cys Thr
1075 1080 1085

Cys Cys Gly Cys Ala Cys Gly Thr Thr Gly Cys Cys Gly Gly Ala Gly
1090 1095 1100

Cys Gly Gly Cys Thr Gly Cys Thr Thr Thr Gly Ala Thr Thr Cys Thr
1105 1110 1115 1120

Thr Thr Cys Thr Ala Ala Gly Cys Ala Cys Cys Cys Gly Ala Ala Cys
1125 1130 1135

Thr Gly Gly Ala Cys Ala Ala Ala Cys Ala Cys Thr Cys Ala Ala Gly
1140 1145 1150

Thr Cys Cys Gly Cys Ala Gly Cys Ala Gly Thr Thr Thr Ala Gly Ala
1155 1160 1165

Ala Ala Ala Cys Ala Cys Cys Ala Cys Thr Ala Cys Ala Ala Ala Ala
1170 1175 1180

Cys Thr Thr Gly Gly Thr Gly Ala Thr Thr Cys Thr Thr Thr Gly Thr
1185 1190 1195 1200

Ala Cys Thr Ala Thr Gly Gly Ala Ala Ala Ala Gly Gly Gly Cys Thr
1205 1210 1215

Gly Ala Thr Cys Ala Ala Cys Gly Thr Ala Cys Ala Ala Gly Cys Gly
1220 1225 1230

Gly Cys Ala Gly Cys Thr Cys Ala Gly Thr Ala Ala Ala Ala Cys Ala
1235 1240 1245

Thr Ala Ala Ala Ala Ala Ala Cys Cys Gly Gly Cys Cys Thr Thr Gly
1250 1255 1260

Gly Cys Cys Cys Cys Gly Cys Cys Gly Gly Thr Thr Thr Thr Thr Thr
1265 1270 1275 1280

Ala Thr Thr Ala Thr Thr Thr Thr Thr Cys Thr Thr Cys Cys Thr Cys
1285 1290 1295

Cys Gly Cys Ala Thr Gly Thr Thr Cys Ala Ala Thr Cys Cys Gly Cys
1300 1305 1310

Thr Cys Cys Ala Thr Ala Ala Thr Cys Gly Ala Cys Gly Gly Ala Thr
1315 1320 1325

Gly Gly Cys Thr Cys Cys Cys Thr Cys Thr Gly Ala Ala Ala Ala Thr
1330 1335 1340

Thr Thr Thr Ala Ala Cys Gly Ala Gly Ala Ala Ala Cys Gly Gly Cys
1345 1350 1355 1360

Gly Gly Gly Thr Thr Gly Ala Cys Cys Cys Gly Gly Cys Thr Cys Ala
1365 1370 1375

Gly Thr Cys Cys Cys Gly Thr Ala Ala Cys Gly Gly Cys Cys Ala Ala
1380 1385 1390

Cys Thr Cys Cys Thr Gly Ala Ala Ala Cys Gly Thr Cys Thr Cys Ala

```
              1395                1400                  1405
   Ala Thr Cys Gly Cys Cys Gly Cys Thr Thr Cys Cys Cys Gly Gly Thr
       1410                1415                1420

Thr Thr Cys Cys Gly Gly Thr Cys Ala Gly Cys Thr Cys Ala Ala Thr
   1425                1430                1435                1440

Gly Cys Cys Ala Thr Ala Ala Cys Gly Gly Thr Cys Gly Gly Cys Gly
               1445                1450                1455

Gly Cys Gly Thr Thr Thr Cys Cys Thr Gly Ala Thr Ala Cys Cys
               1460                1465                1470

Gly Gly Gly Ala Gly Ala Cys Gly Gly Cys Ala Thr Thr Cys Gly Thr
               1475                1480                1485

Ala Ala Thr Cys Gly Gly Ala Thr Cys
               1490                1495

<210> SEQ ID NO 3
<211> LENGTH: 275
<212> TYPE: PRT
<213> ORGANISM: B. amyloliquefaciens

<400> SEQUENCE: 3

Ala Gln Ser Val Pro Tyr Gly Val Ser Gln Ile Lys Ala Pro Ala Leu
   1               5                   10                  15

His Ser Gln Gly Tyr Thr Gly Ser Asn Val Lys Val Ala Val Ile Asp
                   20                  25                  30

Ser Gly Ile Asp Ser Ser His Pro Asp Leu Lys Val Ala Gly Gly Ala
               35                  40                  45

Ser Met Val Pro Ser Glu Thr Asn Pro Phe Gln Asp Asn Asn Ser His
       50                  55                  60

Gly Thr His Val Ala Gly Thr Val Ala Ala Leu Asn Asn Ser Ile Gly
   65                  70                  75                  80

Val Leu Gly Val Ala Pro Ser Ala Ser Leu Tyr Ala Val Lys Val Leu
                   85                  90                  95

Gly Ala Asp Gly Ser Gly Gln Tyr Ser Trp Ile Ile Asn Gly Ile Glu
                   100                 105                 110

Trp Ala Ile Ala Asn Asn Met Asp Val Ile Asn Met Ser Leu Gly Gly
               115                 120                 125

Pro Ser Gly Ser Ala Ala Leu Lys Ala Ala Val Asp Lys Ala Val Ala
       130                 135                 140

Ser Gly Val Val Val Val Ala Ala Ala Gly Asn Glu Gly Thr Ser Gly
   145                 150                 155                 160

Ser Ser Ser Thr Val Gly Tyr Pro Gly Lys Tyr Pro Ser Val Ile Ala
                   165                 170                 175

Val Gly Ala Val Asp Ser Ser Asn Gln Arg Ala Ser Phe Ser Ser Val
                   180                 185                 190

Gly Pro Glu Leu Asp Val Met Ala Pro Gly Val Ser Ile Gln Ser Thr
               195                 200                 205

Leu Pro Gly Asn Lys Tyr Gly Ala Tyr Asn Gly Thr Ser Met Ala Ser
       210                 215                 220

Pro His Val Ala Gly Ala Ala Ala Leu Ile Leu Ser Lys His Pro Asn
   225                 230                 235                 240

Trp Thr Asn Thr Gln Val Arg Ser Ser Leu Glu Asn Thr Thr Thr Lys
                   245                 250                 255

Leu Gly Asp Ser Phe Tyr Tyr Gly Lys Gly Leu Ile Asn Val Gln Ala
                   260                 265                 270
```

-continued

```
Ala Ala Gln
        275

<210> SEQ ID NO 4
<211> LENGTH: 275
<212> TYPE: PRT
<213> ORGANISM: B. subtilis

<400> SEQUENCE: 4

Ala Gln Ser Val Pro Tyr Gly Ile Ser Gln Ile Lys Ala Pro Ala Leu
 1               5                  10                  15

His Ser Gln Gly Tyr Thr Gly Ser Asn Val Lys Val Ala Val Ile Asp
                20                  25                  30

Ser Gly Ile Asp Ser Ser His Pro Asp Leu Asn Val Arg Gly Gly Ala
            35                  40                  45

Ser Phe Val Pro Ser Glu Thr Asn Pro Tyr Gln Asp Gly Ser Ser His
        50                  55                  60

Gly Thr His Val Ala Gly Thr Ile Ala Ala Leu Asn Asn Ser Ile Gly
 65                  70                  75                  80

Val Leu Gly Val Ser Pro Ser Ala Ser Leu Tyr Ala Val Lys Val Leu
                85                  90                  95

Asp Ser Thr Gly Ser Gly Gln Tyr Ser Trp Ile Ile Asn Gly Ile Glu
            100                 105                 110

Trp Ala Ile Ser Asn Asn Met Asp Val Ile Asn Met Ser Leu Gly Gly
        115                 120                 125

Pro Thr Gly Ser Thr Ala Leu Lys Thr Val Val Asp Lys Ala Val Ser
    130                 135                 140

Ser Gly Ile Val Val Ala Ala Ala Gly Asn Glu Gly Ser Ser Gly
145                 150                 155                 160

Ser Thr Ser Thr Val Gly Tyr Pro Ala Lys Tyr Pro Ser Thr Ile Ala
                165                 170                 175

Val Gly Ala Val Asn Ser Ser Asn Gln Arg Ala Ser Phe Ser Ser Ala
            180                 185                 190

Gly Ser Glu Leu Asp Val Met Ala Pro Gly Val Ser Ile Gln Ser Thr
        195                 200                 205

Leu Pro Gly Gly Thr Tyr Gly Ala Tyr Asn Gly Thr Ser Met Ala Thr
    210                 215                 220

Pro His Val Ala Gly Ala Ala Ala Leu Ile Leu Ser Lys His Pro Thr
225                 230                 235                 240

Trp Thr Asn Ala Gln Val Arg Asp Arg Leu Glu Ser Thr Ala Thr Tyr
                245                 250                 255

Leu Gly Asn Ser Phe Tyr Tyr Gly Lys Gly Leu Ile Asn Val Gln Ala
            260                 265                 270

Ala Ala Gln
        275

<210> SEQ ID NO 5
<211> LENGTH: 274
<212> TYPE: PRT
<213> ORGANISM: B. licheniformis

<400> SEQUENCE: 5

Ala Gln Thr Val Pro Tyr Gly Ile Pro Leu Ile Lys Ala Asp Lys Val
 1               5                  10                  15

Gln Ala Gln Gly Phe Lys Gly Ala Asn Val Lys Val Ala Val Leu Asp
                20                  25                  30
```

-continued

Thr Gly Ile Gln Ala Ser His Pro Asp Leu Asn Val Val Gly Gly Ala
         35                  40                  45

Ser Phe Val Ala Gly Glu Ala Tyr Asn Thr Asp Gly Asn Gly His Gly
 50                  55                  60

Thr His Val Ala Gly Thr Val Ala Ala Leu Asp Asn Thr Thr Gly Val
65                  70                  75                  80

Leu Gly Val Ala Pro Ser Val Ser Leu Tyr Ala Val Lys Val Leu Asn
                 85                  90                  95

Ser Ser Gly Ser Gly Ser Tyr Ser Gly Ile Val Ser Gly Ile Glu Trp
             100                 105                 110

Ala Thr Thr Asn Gly Met Asp Val Ile Asn Met Ser Leu Gly Gly Ala
             115                 120                 125

Ser Gly Ser Thr Ala Met Lys Gln Ala Val Asp Asn Ala Tyr Ala Arg
         130                 135                 140

Gly Val Val Val Ala Ala Ala Gly Asn Ser Gly Asn Ser Gly Ser
145                 150                 155                 160

Thr Asn Thr Ile Gly Tyr Pro Ala Lys Tyr Asp Ser Val Ile Ala Val
                 165                 170                 175

Gly Ala Val Asp Ser Asn Ser Asn Arg Ala Ser Phe Ser Ser Val Gly
             180                 185                 190

Ala Glu Leu Glu Val Met Ala Pro Gly Ala Gly Val Tyr Ser Thr Tyr
         195                 200                 205

Pro Thr Asn Thr Tyr Ala Thr Leu Asn Gly Thr Ser Met Ala Ser Pro
210                 215                 220

His Val Ala Gly Ala Ala Ala Leu Ile Leu Ser Lys His Pro Asn Leu
225                 230                 235                 240

Ser Ala Ser Gln Val Arg Asn Arg Leu Ser Ser Thr Ala Thr Tyr Leu
                 245                 250                 255

Gly Ser Ser Phe Tyr Tyr Gly Lys Gly Leu Ile Asn Val Glu Ala Ala
             260                 265                 270

Ala Gln

<210> SEQ ID NO 6
<211> LENGTH: 269
<212> TYPE: PRT
<213> ORGANISM: B. lentus

<400> SEQUENCE: 6

Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                 20                  25                  30

Thr Gly Ile Ser Thr His Pro Asp Leu Asn Ile Arg Gly Gly Ala Ser
             35                  40                  45

Phe Val Pro Gly Glu Pro Ser Thr Gln Asp Gly Asn Gly His Gly Thr
 50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                 85                  90                  95

Ser Gly Ser Gly Ser Val Ser Ser Ile Ala Gln Gly Leu Glu Trp Ala
             100                 105                 110

Gly Asn Asn Gly Met His Val Ala Asn Leu Ser Leu Gly Ser Pro Ser
             115                 120                 125

-continued

```
Pro Ser Ala Thr Leu Glu Gln Ala Val Asn Ser Ala Thr Ser Arg Gly
        130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265

<210> SEQ ID NO 7
<211> LENGTH: 1052
<212> TYPE: PRT
<213> ORGANISM: Homo sapien

<400> SEQUENCE: 7

Met Lys Leu Val Asn Ile Trp Leu Leu Leu Val Leu Leu Cys
1               5                   10                  15

Gly Lys Lys His Leu Gly Asp Arg Leu Glu Lys Ser Phe Glu Lys
            20                  25                  30

Ala Pro Cys Pro Gly Cys Ser His Leu Thr Leu Lys Val Glu Phe Ser
            35                  40                  45

Ser Thr Val Val Glu Tyr Glu Tyr Ile Val Ala Phe Asn Gly Tyr Phe
    50                  55                  60

Thr Ala Lys Ala Arg Asn Ser Phe Ile Ser Ala Leu Lys Ser Ser
65                  70                  75                  80

Glu Val Asp Asn Trp Arg Ile Ile Pro Arg Asn Asn Pro Ser Ser Asp
                85                  90                  95

Tyr Pro Ser Asp Phe Glu Val Ile Gln Ile Lys Glu Lys Gln Lys Ala
                100                 105                 110

Gly Leu Leu Thr Leu Glu Asp His Pro Asn Ile Lys Arg Val Thr Pro
            115                 120                 125

Gln Arg Lys Val Phe Arg Ser Leu Lys Tyr Ala Glu Ser Asp Pro Thr
        130                 135                 140

Val Pro Cys Asn Glu Thr Arg Trp Ser Gln Lys Trp Gln Ser Ser Arg
145                 150                 155                 160

Pro Leu Arg Arg Ala Ser Leu Ser Leu Gly Ser Gly Phe Trp His Ala
                165                 170                 175

Thr Gly Arg His Ser Ser Arg Arg Leu Leu Arg Ala Ile Pro Arg Gln
            180                 185                 190

Val Ala Gln Thr Leu Gln Ala Asp Val Leu Trp Gln Met Gly Tyr Thr
        195                 200                 205

Gly Ala Asn Val Arg Val Ala Val Phe Asp Thr Gly Leu Ser Glu Lys
    210                 215                 220

His Pro His Phe Lys Asn Val Lys Glu Arg Thr Asn Trp Thr Asn Glu
225                 230                 235                 240
```

-continued

```
Arg Thr Leu Asp Asp Gly Leu Gly His Gly Thr Phe Val Ala Gly Val
            245                 250                 255
Ile Ala Ser Met Arg Glu Cys Gln Gly Phe Ala Pro Asp Ala Glu Leu
            260                 265                 270
His Ile Phe Arg Val Phe Thr Asn Asn Gln Val Ser Tyr Thr Ser Trp
            275                 280                 285
Phe Leu Asp Ala Phe Asn Tyr Ala Ile Leu Lys Lys Ile Asp Val Leu
            290                 295                 300
Asn Leu Ser Ile Gly Gly Pro Asp Phe Met Asp His Pro Phe Val Asp
305                 310                 315                 320
Lys Val Trp Glu Leu Thr Ala Asn Asn Val Ile Met Val Ser Ala Ile
                325                 330                 335
Gly Asn Asp Gly Pro Leu Tyr Gly Thr Leu Asn Asn Pro Ala Asp Gln
                340                 345                 350
Met Asp Val Ile Gly Val Gly Gly Ile Asp Phe Glu Asp Asn Ile Ala
                355                 360                 365
Arg Phe Ser Ser Arg Gly Met Thr Thr Trp Glu Leu Pro Gly Gly Tyr
370                 375                 380
Gly Arg Met Lys Pro Asp Ile Val Thr Tyr Gly Ala Gly Val Arg Gly
385                 390                 395                 400
Ser Gly Val Lys Gly Gly Cys Arg Ala Leu Ser Gly Thr Ser Val Ala
                405                 410                 415
Ser Pro Val Ala Gly Ala Val Thr Leu Leu Val Ser Thr Val Gln
                420                 425                 430
Lys Arg Glu Leu Val Asn Pro Ala Ser Met Lys Gln Ala Leu Ile Ala
                435                 440                 445
Ser Ala Arg Arg Leu Pro Gly Val Asn Met Phe Glu Gln Gly His Gly
450                 455                 460
Lys Leu Asp Leu Leu Arg Ala Tyr Gln Ile Leu Asn Ser Tyr Lys Pro
465                 470                 475                 480
Gln Ala Ser Leu Ser Pro Ser Tyr Ile Asp Leu Thr Glu Cys Pro Tyr
                485                 490                 495
Met Trp Pro Tyr Cys Ser Gln Pro Ile Tyr Tyr Gly Gly Met Pro Thr
                500                 505                 510
Val Val Asn Val Thr Ile Leu Asn Gly Met Gly Val Thr Gly Arg Ile
                515                 520                 525
Val Asp Lys Pro Asp Trp Gln Pro Tyr Leu Pro Gln Asn Gly Asp Asn
                530                 535                 540
Ile Glu Val Ala Phe Ser Tyr Ser Ser Val Leu Trp Pro Trp Ser Gly
545                 550                 555                 560
Tyr Leu Ala Ile Ser Ile Ser Val Thr Lys Lys Ala Ala Ser Trp Glu
                565                 570                 575
Gly Ile Ala Gln Gly His Val Met Ile Thr Val Ala Ser Pro Ala Glu
                580                 585                 590
Thr Glu Ser Lys Asn Gly Ala Glu Gln Thr Ser Thr Val Lys Leu Pro
                595                 600                 605
Ile Lys Val Lys Ile Ile Pro Thr Pro Arg Ser Lys Arg Val Leu
                610                 615                 620
Trp Asp Gln Tyr His Asn Leu Arg Tyr Pro Pro Gly Tyr Phe Pro Arg
625                 630                 635                 640
Asp Asn Leu Arg Met Lys Asn Asp Pro Leu Asp Trp Asn Gly Asp His
                645                 650                 655
```

-continued

```
Ile His Thr Asn Phe Arg Asp Met Tyr Gln His Leu Arg Ser Met Gly
        660                 665                 670

Tyr Phe Val Glu Val Leu Gly Ala Pro Phe Thr Cys Phe Asp Ala Ser
            675                 680                 685

Gln Tyr Gly Thr Leu Leu Met Val Asp Ser Glu Glu Glu Tyr Phe Pro
        690                 695                 700

Glu Glu Ile Ala Lys Leu Arg Arg Asp Val Asp Asn Gly Leu Ser Leu
705                 710                 715                 720

Val Ile Phe Ser Asp Trp Tyr Asn Thr Ser Val Met Arg Lys Val Lys
                725                 730                 735

Phe Tyr Asp Glu Asn Thr Arg Gln Trp Trp Met Pro Asp Thr Gly Gly
                740                 745                 750

Ala Asn Ile Pro Ala Leu Asn Glu Leu Leu Ser Val Trp Asn Met Gly
            755                 760                 765

Phe Ser Asp Gly Leu Tyr Glu Gly Glu Phe Thr Leu Ala Asn His Asp
        770                 775                 780

Met Tyr Tyr Ala Ser Gly Cys Ser Ile Ala Lys Phe Pro Glu Asp Gly
785                 790                 795                 800

Val Val Ile Thr Gln Thr Phe Lys Asp Gln Gly Leu Glu Val Leu Lys
                805                 810                 815

Gln Glu Thr Ala Val Val Glu Asn Val Pro Ile Leu Gly Leu Tyr Gln
            820                 825                 830

Ile Pro Ala Glu Gly Gly Gly Arg Ile Val Leu Tyr Gly Asp Ser Asn
        835                 840                 845

Cys Leu Asp Asp Ser His Arg Gln Lys Asp Cys Phe Trp Leu Leu Asp
850                 855                 860

Ala Leu Leu Gln Tyr Thr Ser Tyr Gly Val Thr Pro Pro Ser Leu Ser
865                 870                 875                 880

His Ser Gly Asn Arg Gln Arg Pro Pro Ser Gly Ala Gly Ser Val Thr
                885                 890                 895

Pro Glu Arg Met Glu Gly Asn His Leu His Arg Tyr Ser Lys Val Leu
            900                 905                 910

Glu Ala His Leu Gly Asp Pro Lys Pro Arg Pro Leu Pro Ala Cys Pro
        915                 920                 925

Arg Leu Ser Trp Ala Lys Pro Gln Pro Leu Asn Glu Thr Ala Pro Ser
930                 935                 940

Asn Leu Trp Lys His Gln Lys Leu Leu Ser Ile Asp Leu Asp Lys Val
945                 950                 955                 960

Val Leu Pro Asn Phe Arg Ser Asn Arg Pro Gln Val Arg Pro Leu Ser
                965                 970                 975

Pro Gly Glu Ser Gly Ala Trp Asp Ile Pro Gly Gly Ile Met Pro Gly
            980                 985                 990

Arg Tyr Asn Gln Glu Val Gly Gln Thr Ile Pro Val Phe Ala Phe Leu
        995                 1000                1005

Gly Ala Met Val Val Leu Ala Phe Phe Val Val Gln Ile Asn Lys Ala
        1010                1015                1020

Lys Ser Arg Pro Lys Arg Arg Lys Pro Arg Val Lys Arg Pro Gln Leu
1025                1030                1035                1040

Met Gln Gln Val His Pro Pro Lys Thr Pro Ser Val
                1045                1050
```

HUMAN PROTEASE AND USE OF SUCH PROTEASE FOR PHARMACEUTICAL APPLICATIONS AND FOR REDUCING THE ALLERGENICITY OF NON-HUMAN PROTEINS

BACKGROUND OF THE INVENTION

A. Field of the Invention

The present invention relates to a human protein sequence which can be used in several applications. Specifically, the novel human protein sequence can be used to design proteins which produce lower allergenic response in humans exposed to such proteins through the use of a predictive assay.

B. State of the Art

Serine proteases are a subgroup of carbonyl hydrolases. They comprise a diverse class of enzymes having a wide range of specificities and biological functions. Stroud, R. *Sci. Amer.,* 131:74–88. Despite their functional diversity, the catalytic machinery of serine proteases has been approached by at least two genetically distinct families of enzymes: the subtilisins and the mammalian chymotrypsin related and homologous bacterial serine proteases (e.g., trypsin and *S. gresius* trypsin). These two families of serine proteases show remarkably similar mechanisms of catalysis. Kraut, J. (1977), *Ann. Rev. Biochem.,* 46:331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW 27,500) which is secreted in large amounts from a wide variety of Bacillus species and other microorganisms. The protein sequence of subtilisin has been determined from at least four different species of Bacillus. Markland, F. S., et al. (1983), *Honne-Seyler's Z. Physiol. Chem.,* 364:1537–1540. The three-dimensional crystallographic structure of *Bacillus amyloliquefaciens* subtilisin to 2.5A resolution has also been reported. Wright, C. S., et al. (1969), *Nature,* 221:235–242; Drenth, J., et al. (1972), *Eur. J. Biochem.,* 26:177–181. These studies indicate that although subtilisin is genetically unrelated to the mammalian chymotrypsin like serine proteases, it has a similar active site structure. The x-ray crystal structures of subtilisin containing covalently bound peptide inhibitors (Robertus, J. D., et al. (1972), *Biochemistry,* 11:2439–2449) or product complexes (Robertus, J. D., et al. (1976), *J. Biol. Chem.,* 251:1097–1103) have also provided information regarding the active site and putative substrate binding cleft of subtilisin. In addition, a large number of kinetic and chemical modification studies have been reported for subtilisin (Philipp, M., et al. (1983), *Mol. Cell. Biochem.,* 51:5–32; Svendsen, B. (1976), *Carlsberg Res. Comm.,* 41:237–291; Markland, F. S. *Id.*) as well as at least one report wherein the side chain of methionine at residue 222 of subtilisin was converted by hydrogen peroxide to methionine-sulfoxide (Stauffer, D. C., et al. (1965), *J. Biol. Chem.,* 244:5333–5338) and the side chain of serine at residue 221 converted to cysteine by chemical modification (Polgar, et al. (1981), *Biochimica et Biophysica Acta,* 667:351–354.)

Proteins bearing some resemblance and/or homology to bacterial subtilisin have also been detected in humans as well (see e.g., Keifer et al., *DNA and Cell Biol.,* Vol. 10, No. 10, pp. 757–769 (1991); Smeekens et al.,*J. Biol. Chem.,* Vol. 265, No. 6, pp. 2997–3000 (1990); Tomkinson et al., *Biochem., Vol.* 30, pp. 168–174 (1991)).

U.S. Pat. No. 4,760,025 (RE 34,606) discloses the modification of subtilisin amino acid residues corresponding to positions in Bacillus amyloliquefaciens subtilisin tyrosine −1, aspartate +32, asparagine +155, tyrosine +104, methionine +222, glycine +166, histidine +64, glycine +169, phenylalanine +189, serine +33, serine +221, tyrosine +217, glutamate +156 and alanine +152. U.S. Pat. No. 5,182,204 discloses the modification of the amino acid +224 residue in *Bacillus amyloliquefaciens* subtilisin and equivalent positions in other subtilisins which may be modified by way of substitution, insertion or deletion and which may be combined with modifications to the residues identified in U.S. Pat. No. 4,760,025 (RE 34,606) to form useful subtilisin mutants or variants. U.S. Pat. No. 5,155,033 discloses similar mutant subtilisins having a modification at an equivalent position to +225 of *B. amyloliquefaciens* subtilisin. U.S. Pat. Nos. 5,185,258 and 5,204,015 disclose mutant subtilisins having a modification at positions +123 and/or +274. U.S. Pat. No. 5,182,204 discloses the modification of many amino acid residues within subtilisin, including specifically +99, +101, +103, +107, +126, +128, +135, +197 and +204. U.S. Pat. No. 4,914,031 discloses certain subtilisin analogs, including a subtilisin modified at position +76.

Proteins, including proteases, used in industrial, pharmaceutical and commercial applications are of increasing prevalence. As a result, the increased exposure due to this prevalence has been responsible for some safety hazards caused by the sensitization of certain persons to those peptides, whereupon subsequent exposure causes extreme allergic reactions which can be injurious and even fatal. For example, proteases are known to cause dangerous hypersensitivity in some individuals. As a result, despite the usefulness of proteases in industry, e.g., in laundry detergents, cosmetics, textile treatment etc . . . , and the extensive research performed in the field to provide improved proteases which have, for example, more effective stain removal under detergency conditions, the use of proteases in industry has been problematic due to their ability to produce a hypersensitive allergenic response in some humans.

Much work has been done to alleviate these problems. Among the strategies explored to reduce immunogenic potential of protease use have been improved production processes which reduce potential contact by controlling and minimizing workplace concentrations of dust particles or aerosol carrying airborne protease, improved granulation processes which reduce the amount of dust or aerosol actually produced from the protease product, and improved recovery processes to reduce the level of potentially allergenic contaminants in the final product. However, efforts to reduce the allergenicity of protease, per se, have been relatively unsuccessful. Alternatively, efforts have been made to mask epitopes in protease which are recognized by immunoglobulin E (IgE) in hypersensitive individuals (PCT Publication No. WO 92/10755) or to enlarge or change the nature of the antigenic determinants by attaching polymers or peptides/proteins to the problematic protease.

When an adaptive immune response occurs in an exaggerated or inappropriate form, the individual experiencing the reaction is said to be hypersensitive. Hypersensitivity reactions are the result of normally beneficial immune responses acting inappropriately and sometimes cause inflammatory reactions and tissue damage. They can be provoked by many antigens; and the cause of a hypersensitivity reaction will vary from one individual to the next. Hypersensitivity does not normally manifest itself upon first contact with the antigen, but usually appears upon subsequent contact. One form of hypersensitivity occurs when an IgE response is directed against innocuous environmental antigens, such as pollen, dust-mites or animal dander. The resulting release of pharmacological mediators by IgE-sensitized mast cells produces an acute inflammatory reaction with symptoms such as asthma or rhinitis.

Nonetheless, a strategy comprising modifying the IgE sites will not generally be successful in preventing the cause of the initial sensitization reaction. Accordingly, such strategies, while perhaps neutralizing or reducing the severity of the subsequent hypersensitivity reaction, will not reduce the number or persons actually sensitized. For example, when a person is known to be hypersensitive to a certain antigen, the general, and only safe, manner of dealing with such a situation is to isolate the hypersensitive person from the antigen as completely as possible. Indeed, any other course of action would be dangerous to the health of the hypersensitive individual. Thus, while reducing the danger of a specific protein for a hypersensitive individual is important, for industrial purposes it would be far more valuable to render a protein incapable of initiating the hypersensitivity reaction in the first place.

T-lymphocytes (T-cells) are key players in the induction and regulation of immune responses and in the execution of immunological effector functions. Specific immunity against infectious agents and tumors is known to be dependent on these cells and they are believed to contribute to the healing of injuries. On the other hand, failure to control these responses can lead to auto aggression. In general, antigen is presented to T-cells in the form of antigen presenting cells which, through a variety of cell surface mechanisms, capture and display antigen or partial antigen in a manner suitable for antigen recognition by the T-cell. Upon recognition of a specific epitope by the receptors on the surface of the T-cells (T-cell receptors), the T-cells begin a series of complex interactions, including proliferation, which result in the production of antibody by B-cells. While T-cells and B-cells are both activated by antigenic epitopes which exist on a given protein or peptide, the actual epitopes recognized by these mononuclear cells are generally not identical. In fact, the epitope which activates a T-cell to initiate the creation of immunologic diversity is quite often not the same epitope which is later recognized by B-cells in the course of the immunologic response. Thus, with respect to hypersensitivity, while the specific antigenic interaction between the T-cell and the antigen is a critical element in the initiation of the immune response to antigenic exposure, the specifics of that interaction, i.e., the epitope recognized, is often not relevant to subsequent development of a full blown allergic reaction.

PCT Publication No. WO 96/40791 discloses a process for producing polyalkylene oxide-polypeptide conjugates with reduced allergenicity using polyalkylene oxide as a starting material.

PCT Publication No. WO 97/30148 discloses a polypeptide conjugate with reduced allergenicity which comprises one polymeric carrier molecule having two or more polypeptide molecules coupled covalently thereto.

PCT Publication No. WO 96/17929 discloses a process for producing polypeptides with reduced allergenicity comprising the step of conjugating from 1 to 30 polymolecules to a parent polypeptide.

PCT Publication No. WO 92/10755 discloses a method of producing protein variants evoking a reduced immunogenic response in animals. In this application, the proteins of interest, a series of proteases and variants thereof, were used to immunized rats. The sera from the rats was then used to measure the reactivity of the polyclonal antibodies already produced and present in the immunized sera to the protein of interest and variants thereof. From these results, it was possible to determine whether the antibodies in the preparation were comparatively more or less reactive with the protein and its variants, thus permitting an analysis of which changes in the protein are likely to neutralize or reduce the ability of the Ig to bind. From these tests on rats, the conclusion was arrived at that changing any of subtilisin 309 residues corresponding to 127, 128, 129, 130, 131, 151, 136, 151, 152, 153, 154, 161, 162, 163, 167, 168, 169, 170, 171, 172, 173, 174, 175, 176, 186, 193, 194, 195, 196, 197, 247, 251, 261 will result in a change in the immunological potential.

PCT Publication No. WO 94/10191 discloses low allergenic proteins comprising oligomeric forms of the parent monomeric protein, wherein the oligomer has substantially retained its activity.

The prior art has provided methods of reducing the allergenicity of certain proteins and identification of epitopes which cause allergic reactions in some individuals, the assays used to identify these epitopes generally involving measurement of IgE and IgG antibody in blood sera previously exposed to the antigen. Nonetheless, a need continues for alternate methods of preparing low allergenicity enzymes. Likewise, a need exists for an increased availability of human enzymes which may have use in pharmaceutical applications.

SUMMARY OF THE INVENTION

It is an object of the invention to provide a human protease which can be used in industry as a replacement for bacterial and fungal proteases.

It is an object of the invention to provide a method of making currently used and successful proteases and other proteins more safe by integrating therein sequences derived from human protease analogs.

It is a further object of the invention to provide a human protease which may have application in the pharmaceutical industry.

According to the present invention, a method for reducing the allergenicity of a non-human protein is provided wherein an epitope is identified and replaced with an analogous region within a human subtilisin. In a preferred embodiment the non-human protein is an enzyme, more preferably a protease. In another preferred embodiment, the epitope replaced is a T-cell epitope.

In another embodiment of the present invention, a method for producing the protein of the invention having reduced allergenicity is provided. Preferably, the mutant protein is prepared by modifying a DNA encoding a precursor protein so that the modified DNA encodes the mutant protein of the invention wherein an epitope is replaced with an analogous region from human subtilisin.

In yet another embodiment of the invention, DNA sequences encoding the mutant protein, as well as expression vectors containing such DNA sequences and host cells transformed with such vectors are provided, which host cells are preferably capable of expressing such DNA to produce the mutant protein of the invention either intracellularly or extracellularly.

The mutant protein of the invention is useful in any composition or process in which the protein is generally known to be useful. For example, where the protein is a protease, the reduced allergenicity protease can be used as a component in cleaning products such as laundry detergents and hard surface cleansers, as an aid in the preparation of leather, in the treatment of textiles such as wool and/or silk to reduce felting, as a component in a cosmetic or face cream, and as a component in animal or pet feed to improve the nutritional value of the feed. Similarly, where the protein is an amylase, the reduced allergenicity amylase can be used for the liquefaction of starch, as a component in a dishwashing detergent, for desizing of textiles, in a laundry detergent or any other use for which amylase is useful. Similarly, where the protein is a pharmaceutical composition, its use can be made more safe by reducing the possibility of allergic reaction.

In another embodiment of the invention, the human subtilisin may be used in pharmaceutical applications wherein the protease is used for debridement treatments.

BRIEF DESCRIPTION OF THE DRAWINGS

FIGS. 1A–C illustrates the DNA (SEQ ID:NO 1) and amino acid (SEQ ID:NO 2) sequence for *Bacillus amyloliquefaciens* subtilisin (BPN') and a partial restriction map of this gene.

FIG. 2 illustrates the conserved amino acid residues among subtilisins from *Bacillus amyloliquefaciens* (SEQ ID NO: 2), and *Bacillus lentus* (wild-type)(SEQ ID:NO 3).

FIGS. 3A and 3B illustrate an amino acid sequence alignment of subtilisin type proteases from *Bacillus amyloliquefaciens* (BPN') (SEQ ID NO: 2), *Bacillus subtilis* (SEQ ID NO: 5), *Bacillus licheniformis* (SEQ ID:NO 4) and *Bacillus lentus* (SEQ ID NO: 3). The symbol * denotes the absence of specific amino acid residues as compared to subtilisin BPN'.

FIG. 6 illustrates the amino acid sequence of human subtilisin (SEQ ID:NO 6).

FIGS. 7A, 7B and 7C illustrates the amino acid strings corresponding to peptides derived from the sequence of *Bacillus lentus* protease used in Example 2.

FIGS. 8A, 8B, and 8C illustrate the amino acid strings corresponding to peptides derived from the sequence of human subtilisin used in Example 2.

DETAILED DESCRIPTION OF THE INVENTION

Figure 4:
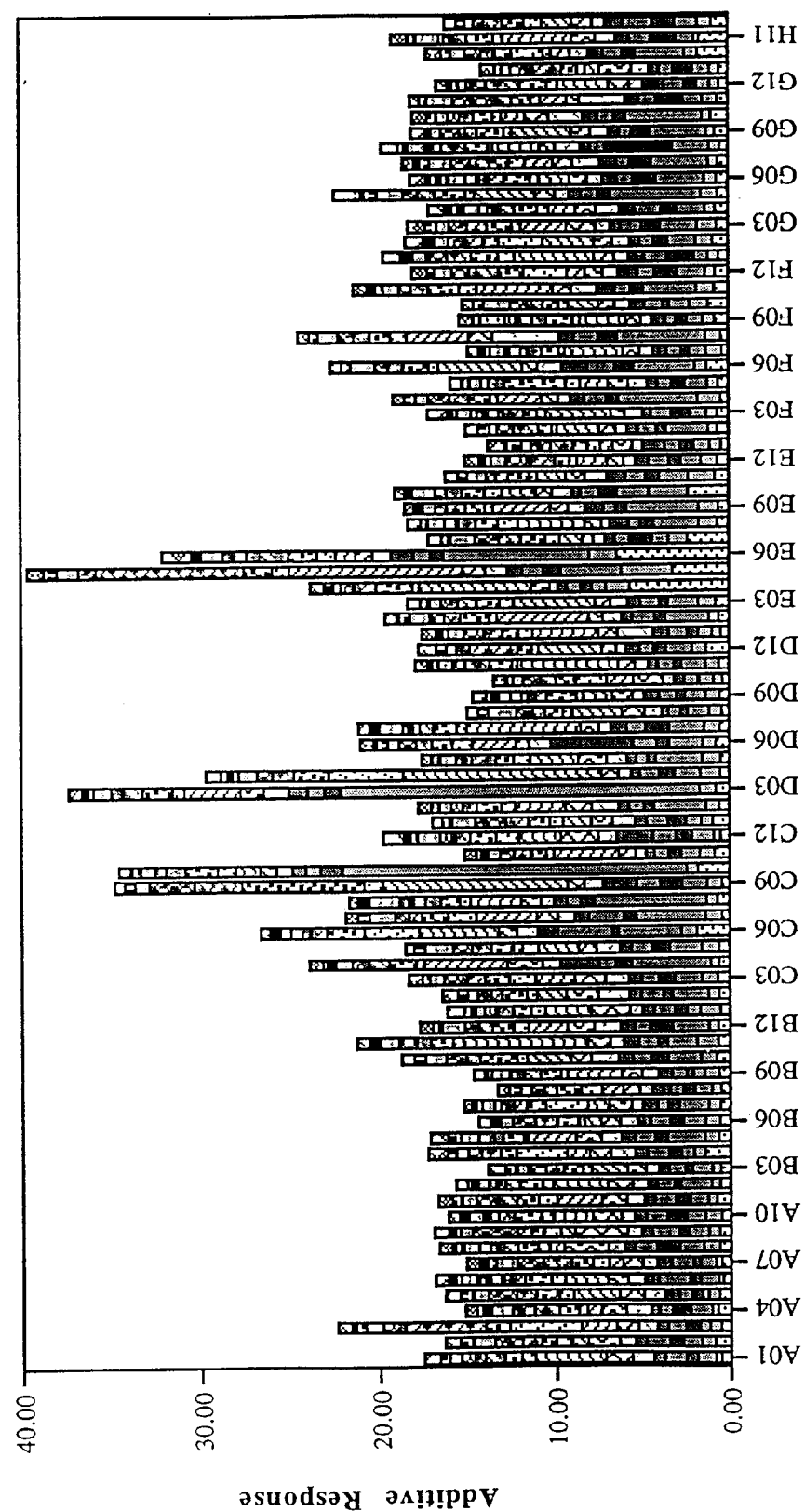
FIG. 4. illustrates the additive T-cell response of 16 peripheral mononuclear blood samples to peptides corresponding to the *Bacillus lentus* protease. Peptide E05 represents the region comprising residues corresponding to 170–173 in protease from *Bacillus amyloliquefaciens*.

According to the present invention, a method for reducing the allergenicity of a non-human protein is provided wherein an epitope is identified and replaced with an analogous region within a human subtilisin. In a preferred embodiment the non-human protein is an enzyme, more preferably a protease. In another preferred embodiment, the epitope replaced is a T-cell epitope.

In another embodiment of the present invention, a method for producing the protein of the invention having reduced allergenicity is provided. Preferably, the mutant protein is prepared by modifying a DNA encoding a precursor protein so that the modified DNA encodes the mutant protein of the invention wherein an epitope is replaced with an analogous region from human subtilisin.

In yet another embodiment of the invention, DNA sequences encoding the mutant protein, as well as expression vectors containing such DNA sequences and host cells transformed with such vectors are provided, which host cells are preferably capable of expressing such DNA to produce the mutant protein of the invention either intracellularly or extracellularly.

According to a preferred embodiment of the present invention, the epitope to be replaced in the non-human protein of interest is identified by a method for identifying T-cell epitopes. In a preferred embodiment of the invention, the present invention provides an assay which identifies epitopes as follows: differentiated dendritic cells are combined with naive human CD4+ and/or CD8+ T-cells and with a peptide of interest. More specifically, a method is provided wherein a T-cell epitope is recognized comprising the steps of: (a) obtaining from a single blood source a solution of dendritic cells and a solution of naive CD4+ and/or CD8+ T-cells; (b) promoting differentiation in said solution of dendritic cells; (c) combining said solution of differentiated dendritic cells and said naive CD4+ and/or CD8+ T-cells with a peptide of interest; (d) measuring the proliferation of T-cells in said step (c).

The non-human peptide of interest to be analyzed according to the assay of the invention is derived from a protein or enzyme for which reduced allergenicity is required. In the practice of the invention, it is possible to identify with precision the location of an epitope which can cause sensitization in an individual or sampling of individuals. In a particularly effective embodiment of the invention, a series of peptide oligomers which correspond to all or part of the protein or enzyme are prepared. For example, a peptide library is produced covering the relevant portion or all of the protein. One particularly useful manner of producing the peptides is to introduce overlap into the peptide library, for example, producing a first peptide corresponds to amino acid sequence 1–10 of the subject protein, a second peptide corresponds to amino acid sequence 4–14 of the subject protein, a third peptide corresponds to amino acid sequence 7–17 of the subject protein, a fourth peptide corresponds to amino acid sequence 10–20 of the subject protein etc . . . until representative peptides corresponding to the entire molecule are created. By analyzing each of the peptides individually in the assay provided herein, it is possible to precisely identify the location of epitopes recognized by T-cells. In the example above, the reaction of one specific peptide to a greater extent than it's neighbors will facilitate identification of the epitope anchor region to within three amino acids. After determining the location of these epitopes, it is possible to alter the amino acids within each epitope until the peptide produces a less significant T-cell response.

Preferably, the epitope is modified in one of the following ways: (a) preferably the amino acid sequence of the epitope is substituted with an analogous sequence from the human subtilisin of the invention to the protein of interest, e.g., where the protein is a subtilisin, a sequence alignment can be arranged so as to find the analogous region in the human subtilisin molecule with which to replace the pertinent epitope in the subtilisin; (b) the amino acid sequence of the epitope is substituted with a sequence from human subtilisin of the invention which substantially mimics the major tertiary structure attributes of the epitope, but which produces a lesser allergenic response due to T-cell epitope recognition than that of the protein of interest; or (c) with any sequence from the human subtilisin of the invention which produces lesser allergenic response due to T-cell epitope recognition than that of the protein of interest.

"Antigen presenting cell" as used herein means a cell of the immune system which present antigen on their surface which is recognizable by T-cells. Examples of antigen presenting cells are dendritic cells, interdigitating cells, activated B-cells and macrophages.

"T-cell proliferation" as used herein means the number of T-cells produced during the incubation of T-cells with the antigen presenting cells, with or without antigen.

"Baseline T-cell proliferation" as used herein means T-cell proliferation which is normally seen in an individual in response to exposure to antigen presenting cells in the absence of peptide or protein antigen. For the purposes herein, the baseline T-cell proliferation level was determined on a per sample basis for each individual as the proliferation of T-cells in response to antigen presenting cells in the absence of antigen.

"T-cell epitope" means a feature of a peptide or protein which is recognized by a T-cell receptor in the initiation of an immunologic response to the peptide comprising that antigen. Recognition of a T-cell epitope by a T-cell is generally believed to be via a mechanism wherein T-cells recognize peptide fragments of antigens which are bound to class I or class II major histocompatability (MHC) molecules expressed on antigen-presenting cells (see e.g., Moeller, G. ed., Antigenic Requirements for Activation of MHC-Restricted Responses, Immunological Review, Volume 98, p 187 (Copenhagen; Munksgaard) (1987).

The epitopes determined according to the assay provided herein are then modified to reduce the allergenic potential of the protein of interest. In a preferred embodiment, the epitope to be modified produces a level of T-cell proliferation of greater than three times the baseline T-cell proliferation in a sample. When modified, the epitope produces less than three times the baseline proliferation, preferably less than two times the baseline proliferation and most preferably less than or substantially equal to the baseline proliferation in a sample.

"Sample" as used herein comprises mononuclear cells which are naive, i.e., not sensitized, to the antigen in question.

"Homolog" as used herein means a protein or enzyme which has similar catalytic action, structure and/or use as the protein of interest. It is desirable to find a homolog that has a tertiary and/or primary structure similar to the protein of interest as replacement of the epitope in the protein of interest with an analogous segment from the homolog will reduce the disruptiveness of the change. Thus, enzymes having significant homology will provide the most desirable target for epitope substitutions with sequences from the human subtilisin of the invention.

An "analogous" sequence may be determined by ensuring that the replacement amino acids show a similar function, the tertiary structure and/or conserved residues to the amino acids in the protein of interest at or near the epitope. Thus, where the epitope region contains, for example, an alpha-helix or a beta-sheet structure, the replacement amino acids should maintain that specific structure.

While the present invention extends to all proteins for which it is desired to reduce allergenicity, for the sake of simplicity, the following will describe a particularly preferred embodiment of the invention, the modification of protease. Proteases are carbonyl hydrolases which generally act to cleave peptide bonds of proteins or peptides. As used herein, "protease" means a naturally-occurring protease or a recombinant protease. Naturally-occurring proteases include α-aminoacylpeptide hydrolase, peptidylamino acid hydrolase, acylamino hydrolase, serine carboxypeptidase, metallocarboxypeptidase, thiol proteinase, carboxylproteinase and metalloproteinase. Serine, metallo, thiol and acid proteases are included, as well as endo and exo-proteases.

Figure 1B-1:
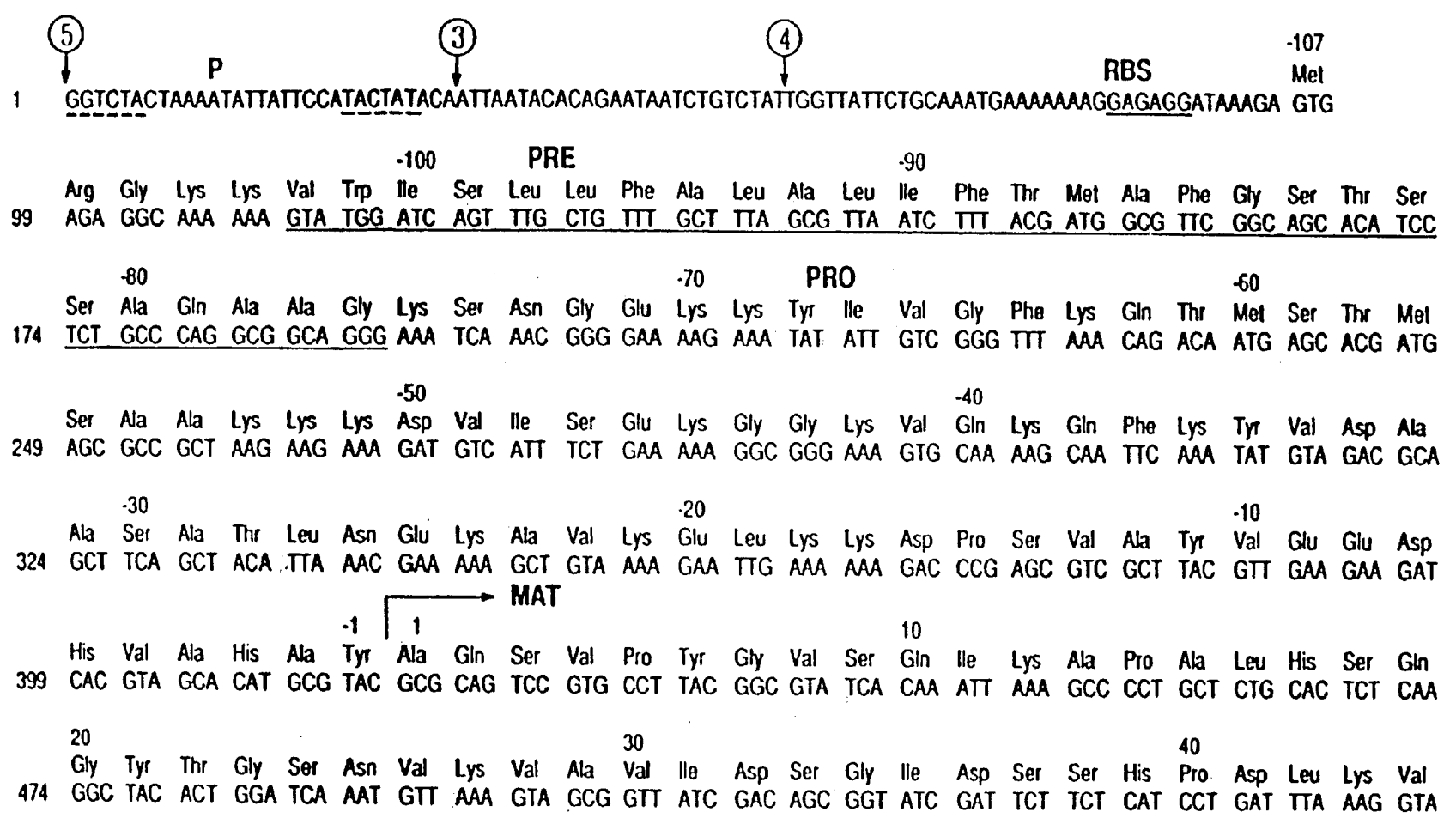

Subtilisins are bacterial or fungal proteases which generally act to cleave peptide bonds of proteins or peptides. As used herein, "subtilisin" means a naturally-occurring subtilisin or a recombinant subtilisin. A series of naturally-occurring subtilisins is known to be produced and often secreted by various microbial species. Amino acid sequences of the members of this series are not entirely homologous. However, the subtilisins in this series exhibit the same or similar type of proteolytic activity. This class of serine proteases shares a common amino acid sequence defining a catalytic triad which distinguishes them from the chymotrypsin related class of serine proteases. The subtilisins and chymotrypsin related serine proteases both have a catalytic triad comprising aspartate, histidine and serine. In the subtilisin related proteases the relative order of these amino acids, reading from the amino to carboxy terminus, is aspartate-histidine-serine. In the chymotrypsin related proteases, the relative order, however, is histidine-aspartate-serine. Thus, subtilisin herein refers to a serine protease having the catalytic triad of subtilisin related proteases. Examples include but are not limited to the subtilisins identified in FIG. 3 herein. Generally and for purposes of the present invention, numbering of the amino acids in proteases corresponds to the numbers assigned to the mature *Bacillus amyloliquefaciens* subtilisin sequence presented in FIG. 1.

"Recombinant subtilisin" or "recombinant protease" refer to a subtilisin or protease in which the DNA sequence encoding the subtilisin or protease is modified to produce a variant (or mutant) DNA sequence which encodes the substitution, deletion or insertion of one or more amino acids in the naturally-occurring amino acid sequence. Suitable methods to produce such modification, and which may be combined with those disclosed herein, include those disclosed in U.S. Pat. Nos. 4,760,025 (RE 34,606), 5,204,015 and 5,185,258.

"Non-human subtilisins" and the DNA encoding them may be obtained from many procaryotic and eucaryotic organisms. Suitable examples of procaryotic organisms include gram negative organisms such as *E. coli* or Pseudomonas and gram positive bacteria such as Micrococcus or Bacillus. Examples of eucaryotic organisms from which subtilisin and their genes may be obtained include yeast such as *Saccharomyces cerevisiae*, fungi such as Aspergillus sp.

"Human subtilisin" means the protein represented by the sequence in FIG. 6, derivatives thereof or modifications thereof which retain the essential ability to hydrolyze peptide bonds.

A "protease variant" has an amino acid sequence which is derived from the amino acid sequence of a "precursor protease". The precursor proteases include naturally-occurring proteases and recombinant proteases. The amino acid sequence of the protease variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor protease rather than manipulation of the precursor protease enzyme per se. Suitable methods for such manipulation of the precursor DNA sequence include methods disclosed herein, as well as methods known to those skilled in the art (see, for example, EP 0 328299, WO89/06279 and the US patents and applications already referenced herein).

These amino acid position numbers used herein refer to those assigned to the mature *Bacillus amyloliquefaciens* subtilisin sequence presented in FIG. 1. The invention, however, is not limited to the mutation of this particular subtilisin but extends to precursor proteases containing amino acid residues at positions which are "equivalent" to the particular identified residues in *Bacillus amyloliquefaciens* subtilisin. In a preferred embodiment of the present invention, the precursor protease is *Bacillus lentus* subtilisin and the substitutions, deletions or insertions are made at the equivalent amino acid residue in *B. lentus* corresponding to those listed above.

A residue (amino acid) of a precursor protease is equivalent to a residue of *Bacillus amyloliquefaciens* subtilisin if it is either homologous (i.e., corresponding in position in either primary or tertiary structure) or analogous to a specific residue or portion of that residue in *Bacillus amyloliquefaciens* subtilisin (i.e., having the same or similar functional capacity to combine, react, or interact chemically).

In order to establish homology to primary structure, the amino acid sequence of a precursor protease is directly compared to the *Bacillus amyloliquefaciens*subtilisin primary sequence and particularly to a set of residues known to be invariant in subtilisins for which sequence is known. For example, FIG. 2 herein shows the conserved residues as between *B. amyloliquefaciens* subtilisin and *B. lentus* subtilisin. After aligning the conserved residues, allowing for necessary insertions and deletions in order to maintain alignment (i.e., avoiding the elimination of conserved residues through arbitrary deletion and insertion), the residues equivalent to particular amino acids in the primary sequence of *Bacillus amyloliquefaciens* subtilisin are defined. Alignment of conserved residues preferably should conserve 100% of such residues. However, alignment of greater than 75% or as little as 50% of conserved residues is also adequate to define equivalent residues. Conservation of the catalytic triad, Asp32/His64/Ser221 should be maintained.

For example, in FIG. 6 the amino acid sequence of subtilisin from Bacillus amyloliquefaciens, *Bacillus subtilis, Bacillus licheniformis* (carlsbergensis) and *Bacillus lentus* are aligned to provide the maximum amount of homology between amino acid sequences. A comparison of these sequences shows that there are a number of conserved residues contained in each sequence. These conserved residues (as between BPN' and *B. lentus*) are identified in FIG. 2.

Figures 3, 3A, 3B:
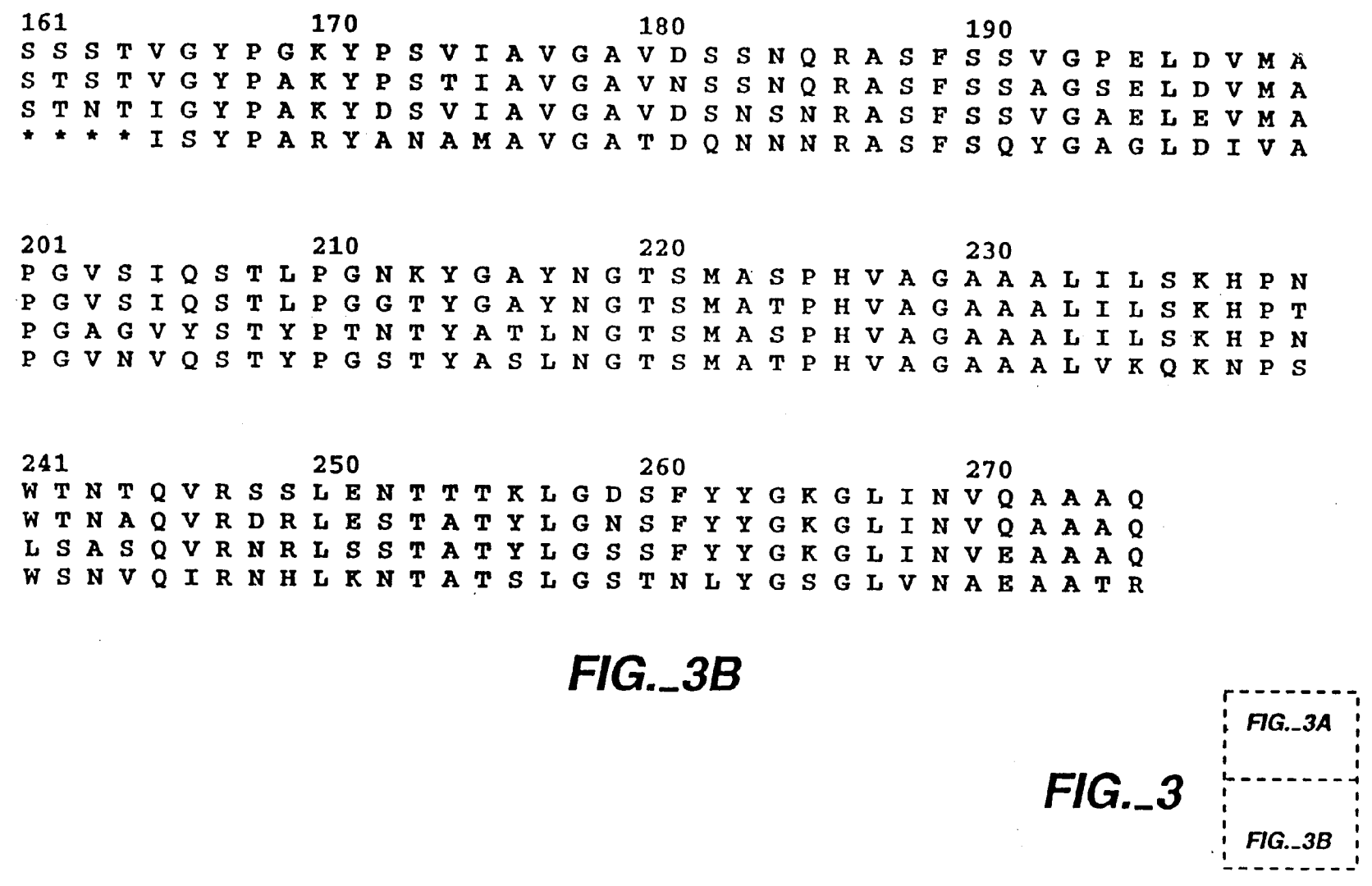

These conserved residues, thus, may be used to define the corresponding equivalent amino acid residues of *Bacillus amyloliquefaciens* subtilisin in other subtilisins such as subtilisin from *Bacillus lentus* (PCT Publication No. WO89/06279 published Jul. 13, 1989), the preferred protease precursor enzyme herein, or the subtilisin referred to as PB92 (EP 0 328 299), which is highly homologous to the preferred *Bacillus lentus* subtilisin. The amino acid sequences of certain of these subtilisins are aligned in FIGS. 3A and 3B with the sequence of *Bacillus amyloliquefaciens* subtilisin to produce the maximum homology of conserved residues. As can be seen, there are a number of deletions in the sequence of *Bacillus lentus* as compared to *Bacillus amyloliquefaciens* subtilisin. Thus, for example, the equivalent amino acid for Vail 65 in *Bacillus amyloliquefaciens* subtilisin in the other subtilisins is isoleucine for *B. lentus* and *B. licheniformis*.

Thus, for example, the amino acid at position +170 is lysine (K) in both *B. amyloliquefaciens* and *B. licheniformis* subtilisins and arginine (R) in Savinase. In the protease variants of the invention, however, the amino acid equivalent to +170 in *Bacillus amyloliquefaciens* subtilisin is substituted with aspartic acid (D). The abbreviations and one letter codes for all amino acids in the present invention conform to the PatentIn User Manual (GenBank, Mountain View, Calif.) 1990, p. 101.

"Equivalent residues" may also be defined by determining homology at the level of tertiary structure for a precursor protease whose tertiary structure has been determined by x-ray crystallography. Equivalent residues are defined as those for which the atomic coordinates of two or more of the main chain atoms of a particular amino acid residue of the precursor protease and *Bacillus amyloliquefaciens* subtilisin (N on N, CA on CA, C on C and O on O) are within 0.13 nm and preferably 0.1 nm after alignment. Alignment is achieved after the best model has been oriented and positioned to give the maximum overlap of atomic coordinates of non-hydrogen protein atoms of the protease in question to the *Bacillus amyloliquefaciens* subtilisin. The best model is the crystallographic model giving the lowest R factor for experimental diffraction data at the highest resolution available.

$$Rfactor = \frac{\sum_h |Fo(h)| - |Fc(h)|}{\sum_h |Fo(h)|}$$

Equivalent residues which are functionally analogous to a specific residue of *Bacillus amyloliquefaciens* subtilisin are defined as those amino acids of the precursor protease which may adopt a conformation such that they either alter, modify or contribute to protein structure, substrate binding or catalysis in a manner defined and attributed to a specific residue of the *Bacillus amyloliquefaciens* subtilisin. Further, they are those residues of the precursor protease (for which a tertiary structure has been obtained by x-ray crystallography) which occupy an analogous position to the extent that, although the main chain atoms of the given residue may not satisfy the criteria of equivalence on the basis of occupying a homologous position, the atomic coordinates of at least two of the side chain atoms of the residue lie with 0.13 nm of the corresponding side chain atoms of Bacillus amyloliquefaciens subtilisin. The coordinates of the three dimensional structure of *Bacillus amyloliquefaciens* subtilisin are set forth in EPO Publication No. 0 251 446 (equivalent to U.S. Pat. No. 5,182,204, the disclosure of which is incorporated herein by reference) and can be used as outlined above to determine equivalent residues on the level of tertiary structure.

Some of the residues identified for substitution, insertion or deletion are conserved residues whereas others are not. In the case of residues which are not conserved, the replacement of one or more amino acids is limited to substitutions which produce a variant which has an amino acid sequence that does not correspond to one found in nature. In the case of conserved residues, such replacements should not result in a naturally-occurring sequence. The protease variants of the present invention include the mature forms of protease variants, as well as the pro- and prepro-forms of such protease variants. The prepro-forms are the preferred construction since this facilitates the expression, secretion and maturation of the protease variants.

"Prosequence" refers to a sequence of amino acids bound to the N-terminal portion of the mature form of a protease which when removed results in the appearance of the "mature" form of the protease. Many proteolytic enzymes are found in nature as translational proenzyme products and, in the absence of post-translational processing, are expressed in this fashion. A preferred prosequence for producing protease variants is the putative prosequence of *Bacillus amyloliquefaciens* subtilisin, although other protease prosequences may be used.

A "signal sequence" or "presequence" refers to any sequence of amino acids bound to the N-terminal portion of a protease or to the N-terminal portion of a proprotease which may participate in the secretion of the mature or pro forms of the protease. This definition of signal sequence is a functional one, meant to include all those amino acid sequences encoded by the N-terminal portion of the protease gene which participate in the effectuation of the secretion of protease under native conditions. The present invention utilizes such sequences to effect the secretion of the protease variants as defined herein. One possible signal sequence comprises the first seven amino acid residues of the signal sequence from *Bacillus subtilis* subtilisin fused to the remainder of the signal sequence of the subtilisin from *Bacillus lentus* (ATCC 21536).

A "prepro" form of a protease variant consists of the mature form of the protease having a prosequence operably linked to the amino terminus of the protease and a "pre" or "signal" sequence operably linked to the amino terminus of the prosequence.

"Expression vector" refers to a DNA construct containing a DNA sequence which is operably linked to a suitable control sequence capable of effecting the expression of said DNA in a suitable host. Such control sequences include a promoter to effect transcription, an optional operator sequence to control such transcription, a sequence encoding suitable mRNA ribosome binding sites and sequences which control termination of transcription and translation. The vector may be a plasmid, a phage particle, or simply a potential genomic insert. Once transformed into a suitable host, the vector may replicate and function independently of the host genome, or may, in some instances, integrate into the genome itself. In the present specification, "plasmid" and "vector" are sometimes used interchangeably as the plasmid is the most commonly used form of vector at present. However, the invention is intended to include such other forms of expression vectors which serve equivalent functions and which are, or become, known in the art.

The "host cells" used in the present invention generally are procaryotic or eucaryotic hosts which preferably have been manipulated by the methods disclosed in U.S. Pat. No. 4,760,025 (RE 34,606) to render them incapable of secreting enzymatically active endoprotease. A preferred host cell for expressing protease is the Bacillus strain BG2036 which is deficient in enzymatically active neutral protease and alkaline protease (subtilisin). The construction of strain BG2036 is described in detail in U.S. Pat. No. 5,264,366. Other host cells for expressing protease include *Bacillus subtilis* 1168 (also described in U.S. Pat. No. 4,760,025 (RE 34,606) and U.S. Pat. No. 5,264,366, the disclosure of which are incorporated herein by reference), as well as any suitable Bacillus strain such as *B. licheniformis, B. lentus,* etc.

Host cells are transformed or transfected with vectors constructed using recombinant DNA techniques. Such transformed host cells are capable of either replicating vectors encoding the protease variants or expressing the desired protease variant. In the case of vectors which encode the pre- or prepro-form of the protease variant, such variants, when expressed, are typically secreted from the host cell into the host cell medium.

"Operably linked, " when describing the relationship between two DNA regions, simply means that they are functionally related to each other. For example, a presequence is operably linked to a peptide if it functions as a signal sequence, participating in the secretion of the mature form of the protein most probably involving cleavage of the signal sequence. A promoter is operably linked to a coding sequence if it controls the transcription of the sequence; a ribosome binding site is operably linked to a coding sequence if it is positioned so as to permit translation.

The genes encoding the naturally-occurring precursor protease may be obtained in accord with the general methods known to those skilled in the art. The methods generally comprise synthesizing labeled probes having putative sequences encoding regions of the protease of interest, preparing genomic libraries from organisms expressing the protease, and screening the libraries for the gene of interest by hybridization to the probes. Positively hybridizing clones are then mapped and sequenced.

The cloned protease is then used to transform a host cell in order to express the protease. The protease gene is then ligated into a high copy number plasmid. This plasmid replicates in hosts in the sense that it contains the well-known elements necessary for plasmid replication: a promoter operably linked to the gene in question (which may be supplied as the gene's own homologous promoter if it is recognized, i.e., transcribed, by the host), a transcription termination and polyadenylation region (necessary for stability of the mRNA transcribed by the host from the protease gene in certain eucaryotic host cells) which is exogenous or is supplied by the endogenous terminator region of the protease gene and, desirably, a selection gene such as an antibiotic resistance gene that enables continuous cultural maintenance of plasmid-infected host cells by growth in antibiotic-containing media. High copy number plasmids also contain an origin of replication for the host, thereby enabling large numbers of plasmids to be generated in the cytoplasm without chromosomal limitations. However, it is within the scope herein to integrate multiple copies of the protease gene into host genome. This is facilitated by procaryotic and eucaryotic organisms which are particularly susceptible to homologous recombination.

In one embodiment, the gene can be a natural gene such as that from *B lentus* or *B. amyloliquefaciens*. Alternatively, a synthetic gene encoding a naturally-occurring or mutant precursor protease may be produced. In such an approach, the DNA and/or amino acid sequence of the precursor protease is determined. Multiple, overlapping synthetic single-stranded DNA fragments are thereafter synthesized, which upon hybridization and ligation produce a synthetic DNA encoding the precursor protease. An example of synthetic gene construction is set forth in Example 3 of U.S. Pat. No. 5,204,015, the disclosure of which is incorporated herein by reference.

Once the naturally-occurring or synthetic precursor protease gene has been cloned, a number of modifications are undertaken to enhance the use of the gene beyond synthesis of the naturally-occurring precursor protease. Such modifications include the production of recombinant proteases as disclosed in U.S. Pat. No. 4,760,025 (RE 34,606) and EPO Publication No. 0 251 446 and the production of protease variants described herein.

The following cassette mutagenesis method may be used to facilitate the construction of the protease variants of the present invention, although other methods may be used. First, the naturally-occurring gene encoding the protease is obtained and sequenced in whole or in part. Then the sequence is scanned for a point at which it is desired to make a mutation (deletion, insertion or substitution) of one or more amino acids in the encoded enzyme. The sequences flanking this point are evaluated for the presence of restriction sites for replacing a short segment of the gene with an oligonucleotide pool which when expressed will encode various mutants. Such restriction sites are preferably unique sites within the protease gene so as to facilitate the replacement of the gene segment. However, any convenient restriction site which is not overly redundant in the protease gene may be used, provided the gene fragments generated by restriction digestion can be reassembled in proper sequence. If restriction sites are not present at locations within a convenient distance from the selected point (from 10 to 15 nucleotides), such sites are generated by substituting nucleotides in the gene in such a fashion that neither the reading frame nor the amino acids encoded are changed in the final construction. Mutation of the gene in order to change its sequence to conform to the desired sequence is accomplished by M13 primer extension in accord with generally known methods. The task of locating suitable flanking regions and evaluating the needed changes to arrive at two convenient restriction site sequences is made routine by the redundancy of the genetic code, a restriction enzyme map of the gene and the large number of different restriction enzymes. Note that if a convenient flanking restriction site is available, the above method need be used only in connection with the flanking region which does not contain a site.

Once the naturally-occurring DNA or synthetic DNA is cloned, the restriction sites flanking the positions to be mutated are digested with the cognate restriction enzymes and a plurality of end termini-complementary oligonucleotide cassettes are ligated into the gene. The mutagenesis is simplified by this method because all of the oligonucleotides can be synthesized so as to have the same restriction sites, and no synthetic linkers are necessary to create the restriction sites.

In one aspect of the invention, the objective is to secure a variant protease having altered allergenic potential as compared to the precursor protease, since decreasing such potential enables safer use of the enzyme. While the instant invention is useful to lower allergenic potential, the mutations specified herein may be utilized in combination with mutations known in the art to result altered thermal stability and/or altered substrate specificity, modified activity or altered alkaline stability as compared to the precursor.

Thus, in combination with the mutations of the present invention, substitutions at positions corresponding to N76D/S103A/V104I/G159D optionally in combination with one or more substitutions selected from the group consisting of positions corresponding to V68A, T213R, A232V, Q236H, Q245R, and T260A of *Bacillus amyloliquefaciens* subtilisin may be used, in addition to decreasing the allergenic potential of the variant protease of the invention, to modulate overall stability and/or proteolytic activity of the enzyme. Similarly, the substitutions provided herein may be combined with mutation at the Asparagine (N) in *Bacillus lentus* subtilisin at equivalent position +76 to Aspartate (D) in combination with the mutations S103A/V104I/G159D and optionally in combination with one or more substitutions selected from the group consisting of positions corresponding to V68A, T213R, A232V, Q236H, Q245R, and T260A of *Bacillus amyloliquefaciens* subtilisin, to produce enhanced stability and/or enhanced activity of the resulting mutant enzyme.

Based on the screening results obtained with the variant proteases, the noted mutations in *Bacillus amyloliquefaciens* subtilisin are important to the proteolytic activity, performance and/or stability of these enzymes and the cleaning or wash performance of such variant enzymes.

Many of the protease variants of the invention are useful in formulating various detergent compositions. A number of known compounds are suitable surfactants useful in compositions comprising the protease mutants of the invention. These include nonionic, anionic, cationic, anionic or zwitterionic detergents, as disclosed in U.S. Pat. No. 4,404,128 to Barry J. Anderson and U.S. Pat. No. 4,261,868 to Jiri Flora, et al. A suitable detergent formulation is that described in Example 7 of U.S. Pat. No. 5,204,015 (previously incorporated by reference). The art is familiar with the different formulations which can be used as cleaning compositions. In addition to typical cleaning compositions, it is readily understood that the protease variants of the present invention may be used for any purpose that native or wild-type proteases are used. Thus, these variants can be used, for example, in personal care items such as face lotions and cosmetics, in bar or liquid soap applications, dishcare formulations, contact lens cleaning solutions or products, peptide hydrolysis, waste treatment, textile applications, as fusion-cleavage enzymes in protein production, etc. The variants of the present invention may comprise enhanced performance in a detergent composition (as compared to the precursor). As used herein, enhanced performance in a detergent is defined as increasing cleaning of certain enzyme sensitive stains such as grass or blood, as determined by usual evaluation after a standard wash cycle.

Proteases of the invention can be formulated into known powdered and liquid detergents having pH between 6.5 and 12.0 at levels of about 0.01 to about 5% (preferably 0.1% to 0.5%) by weight. These detergent cleaning compositions can also include other enzymes such as known proteases, amylases, cellulases, lipases or endoglycosidases, as well as builders and stabilizers.

The addition of proteases of the invention to conventional cleaning compositions does not create any special use limitation. In other words, any temperature and pH suitable for the detergent is also suitable for the present compositions as long as the pH is within the above range, and the temperature is below the described protease's denaturing temperature. In addition, proteases of the invention can be used in a cleaning composition without detergents, again either alone or in combination with builders and stabilizers.

The variant proteases of the present invention can be included in animal feed such as part of animal feed additives as described in, for example, U.S. Pat. No. 5,612,055; U.S. Pat. No. 5,314,692; and U.S. Pat. No. 5,147,642.

One aspect of the invention is a composition for the treatment of a textile that includes variant proteases of the present invention. The composition can be used to treat for example silk or wool as described in publications such as RD 216,034; EP 134,267; U.S. Pat. No. 4,533,359; and EP 344,259.

The following is presented by way of example and is not to be construed as a limitation to the scope of the claims. All publications and patents referenced herein are hereby incorporated by reference in their entirety.

EXAMPLES

Example 1

Assay for the Identification of Peptide T-Cell Epitopes Using Naive Human T-Cells Fresh human peripheral blood cells were collected from "naive" humans, i.e., persons not known to be exposed to or sensitized to *Bacillus lentus* protease, for determination of antigenic epitopes in protease from *Bacillus lentus* and human subtilisin. Naive humans is intended to mean that the individual is not known to have been exposed to or developed a reaction to protease in the past. Peripheral mononuclear blood cells (stored at room temperature, no older than 24 hours) were prepared for use as follows: Approximately 30 mls of a solution of buffy coat preparation from one unit of whole blood was brought to 50 ml with Dulbecco's phosphate buffered solution (DPBS) and split into two tubes. The samples were underlaid with 12.5 ml of room temperature lymphoprep density separation media (Nycomed density 1.077 g/ml). The tubes were centrifuged for thirty minutes at 600G. The interface of the two phases was collected, pooled and washed in DPBS. The cell density of the resultant solution was measured by hemocytometer. Viability was measured by trypan blue exclusion.

From the resulting solution, a differentiated dendritic cell culture was prepared from the peripheral blood mononuclear cell sample having a density of $10^8$ cells per 75 ml culture flask in a solution as follows:

(1) 50 ml of serum free AIM V media (Gibco) was supplemented with a 1:100 dilution beta-mercaptoethanol (Gibco). The flasks were laid flat for two hours at 37° C. in 5% $CO_2$ to allow adherence of monocytes to the flask wall.

(2) Differentiation of the monocyte cells to dendritic cells was as follows: nonadherent cells were removed and the resultant adherent cells (monocytes) combined with 30 ml of AIM V, 800 units/ml of GM-CSF (Endogen) and 500 units/ml of IL-4 (Endogen); the resulting mixture was cultured for 5 days under conditions at 37° C. in 5% $CO_2$. After five days, the cytokine TNF($\alpha$) (Endogen) was added to 0.2 units/ml, and the cytokine IL-1$\alpha$ (Endogen) was added to a final concentration of 50 units/ml and the mixture incubated at 37° C. in 5% $CO_2$ for two more days.

(3) On the seventh day, Mitomycin C was added to a concentration of 50 microgram/ml was added to stop growth of the now differentiated dendritic cell culture. The solution was incubated for 60 minutes at 37° C. in 5% $CO_2$. Dendritic cells were collected by gently scraping the adherent cells off the bottom of the flask with a cell scraper. Adherent and non-adherent cells were then centrifuged at 600G for 5 minutes, washed in DPBS and counted.

(4) The prepared dendritic cells were placed into a 96 well round bottom array at $2\times10^4$/well in 100 microliter total volume.

CD4+ T cells were prepared from frozen aliquots of the peripheral blood cell samples used to prepare the dendritic cells using the human CD4+ Cellect Kit (Biotex) as per the manufacturers instructions with the following modifications: the aliquots were thawed and washed such that approximately $10^8$ cells will be applied per Cellect column; the cells were resuspended in 4 ml DPBS and 1 ml of the Cell reagent from the Cellect Kit, the solution maintained at room temperature for 20 minutes. The resultant solution was centrifuged for five minutes at 600G at room temperature and the pellet resuspended in 2 ml of DPBS and applied to the Cellect columns. The effluent from the columns was collected in 2% human serum in DPBS. The resultant CD4+ cell solution was centrifuged, resuspended in AIMV media and the density counted.

The CD4+ T-cell suspension was resuspended to a count of $2\times10^6$/ml in AIM V media to facilitate efficient manipulation of the 96 well plate.

Peptide antigen is prepared from a 1M stock solution in DMSO by dilution in AIM V media at a 1:10 ratio. 10 microliters of the stock solution is placed in each well of the 96 well plate containing the differentiated dendritic cells. 100 microliter of the diluted CD4+ T-cell solution as prepared above is further added to each well. Useful controls include diluted DMSO blanks, and tetanus toxoid positive controls.

The final concentrations in each well, at 210 microliter total volume are as follows:

$2\times10^5$ CD4+

$2\times10^4$ dendtritic cells (R:S of 10:1)

5 mM/$10^4$ peptide

Example 2

Identification of T-Cell Epitopes in Protease from *Bacillus lentus* and Human subtilisin Peptides for use in the assay described in Example 1 were prepared based on the *Bacillus lentus* and human subtilisin amino acid sequence. Peptide antigens were designed as follows. From the full length amino acid sequence of either human subtilisin or *Bacillus lentus* protease provided in FIG. 1, 15mers were synthetically prepared, each 15 mer overlapping with the previous and the subsequent 15 mer except for three residues.

Peptides used correspond to amino acid residue strings in *Bacillus lentus* as provided in FIG. 7, and peptides correspond to amino acid residues in human subtilisin as provided in FIG. 8. The key for the coded results is provided in FIG. 10. All tests were performed at least in duplicate. All tests reported displayed robust positive control responses to the antigen tetanus toxoid. Responses were averaged within each experiment, then normalized to the baseline response. A positive event was recorded if the response was at least 3 times the baseline response.

Figure 5:
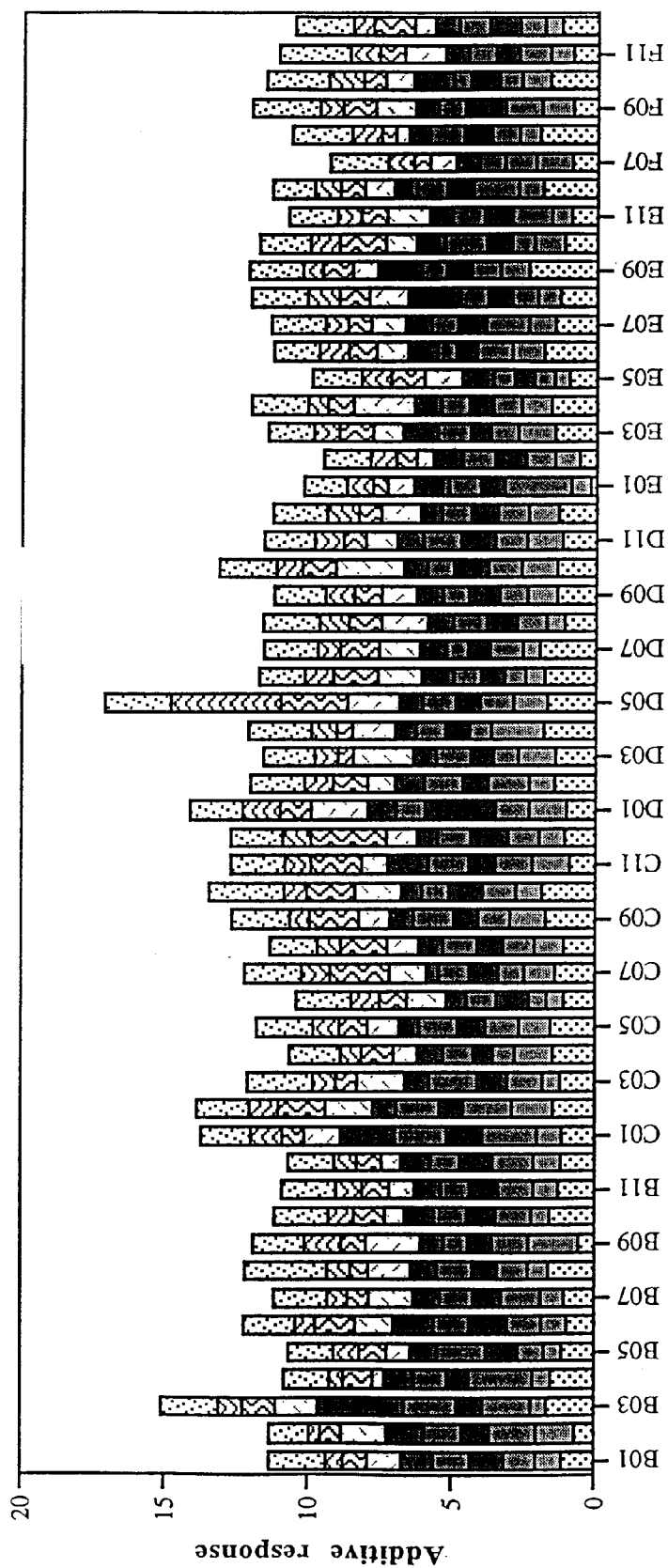
FIG. 5 illustrate the additive T-cell response of 10 peripheral mononuclear blood sample to peptides corresponding to the human subtilisin.

The immunogenic response (i.e., T-cell proliferation) to the prepared peptides from human subtilisin and *Bacillus lentus* was tallied and is provided in FIGS. 4 and 5, respectively. T-cell proliferation was measured by the incorporated tritium method. The results shown in FIGS. 4 and 5 as a comparison of the immunogenic additive response in 10 individuals (FIG. 4) and 16 individuals (FIG. 5) to the various peptides. Response is indicated as the added response wherein 1.0 equals a baseline response for each sample. Thus, in FIG. 4, a reading of 10.0 or less is the baseline response and in FIG. 5 a reading of 16.0 or less the baseline response.

As indicated in FIGS. 4 and 5, the immunogenic response of the naive blood samples from unsensitized individuals showed a marked allergenic response at the peptide fragment from *Bacillus lentus* corresponding to residues 170–173 of *Bacillus amyloliquefaciens* protease. As expected, the corresponding fragment in human subtilisin evokes merely baseline response.

We claim:

1. A method for producing a mutant protease having reduced allergenicity comprising the steps of:
   a) obtaining a naturally-occurring protease having subtilisin activity and preparing fragments of said naturally-occurring protease having subtilisin activity;
   b) contacting said fragments of said naturally-occurring protease with a first solution comprising naïve human CD4+ or CD8+ T-cells and dendritic cells, wherein said dendritic cells have been differentiated;
   c) identifying an epitope region of said naturally-occurring protease, wherein said identifying comprises measuring the ability of said fragments of said naturally-occurring protease epitope region to stimulate proliferation of said naïve human CD4+ or CD8+ T-cells;
   d) replacing said epitope region identified in step c) with an analogous epitope region in the amino acid sequence set forth in SEQ ID NO:6, to produce said mutant protease;
   e) preparing fragments of said mutant protease;
   f) contacting said fragments of said mutant protease with a second solution comprising naïve human CD4+ or CD8+ T-cells and dendritic cells, wherein said dendritic cells have been differentiated; and
   g) measuring the ability of said fragments of said mutant protease to stimulate proliferation of said naïve human CD4+ or CD8+ T-cells.

2. The method of claim 1, further comprising the step of comparing the ability of said fragments of said naturally-occurring protease having microbial subtilisin activity to stimulate proliferation of said naïve human CD4+ or CD8+ T-cells with the ability of said fragments of said mutant protease to stimulate proliferation of said naïve human CD4+ or CD8+ T-cells.

3. The method of claim 1, wherein said dendritic cells and said CD4+ or CD8+ T-cells in said first and second solutions are obtained from a single blood source.

4. The method of claim 1, wherein said naturally-occurring protease is obtained from a Bacillus selected from the group consisting of *B. amyloliquefaciens, B. subtilis, B. licheniformis, B. lentus,* and B. PB92.

5. The method of claim 1, wherein said epitope is a T-cell epitope.

6. The method of claim 1, further comprising the step of producing an expression vector comprising a nucleic acid sequence encoding said mutant protease.

7. The method of claim 6, further comprising the step of transforming at least one host cell with said expression vector.

8. The method of claim 7, further comprising the steps of cultivating said at least one host cell in a culture medium under conditions that promote the expression of said mutant protease and recovering said mutant protease from said cell or said culture medium.

9. A method for reducing the allergenicity of a microbial subtilisin comprising the steps of:
   a) obtaining a microbial subtilisin, and preparing fragments of said microbial subtilisin;
   b) contacting said fragments of said microbial subtilisin with a first solution comprising naïve human CD4+ or CD8+ T-cells and dendritic cells, wherein said dendritic cells have been differentiated;
   c) identifying an epitope of said microbial subtilisin, wherein said identifying comprises measuring the ability of said fragments of said microbial subtilisin to stimulate proliferation of said naïve human CD4+ or CD8+ T-cells;
   d) replacing said epitope identified in step c) with an analogous region in the amino acid sequence set forth in SEQ ID NO:6, to produce a mutant subtilisin;
   e) preparing fragments of said mutant subtilisin;
   f) contacting said fragments of said mutant subtilisin with a second solution comprising naïve human CD4+ or CD8+ T-cells and dendritic cells, wherein said dendritic cells have been differentiated; and
   g) measuring the ability of said fragments of said mutant subtilisin to stimulate proliferation of said naïve human CD4+ or CD8+ T-cells, wherein at least one of said fragments of said mutant subtilisin stimulate said T-cells in said second solution to a lesser extent than the subtilisin in step c).

10. The method of claim 9, wherein said dendritic cells and said CD4+ or CD8+ T-cells in said first and second solutions are obtained from a single blood source.

11. The method of claim 9, wherein said subtilisin is obtained from a Bacillus selected from the group consisting of *B. amyloliquefaciens, B. subtilis, B. licheniformis, B. lentus,* and B. PB92.

12. The method of claim 9, wherein said epitope is a T-cell epitope.

13. The method of claim 9, further comprising the step of producing an expression vector comprising a nucleic acid sequence encoding said mutant subtilisin.

14. The method of claim 13, further comprising the step of transforming at least one host cell with said expression vector.

15. The method of claim 14, further comprising the step of cultivating said at least one host cell in a culture medium under conditions that promote the expression of said mutant protease and recovering said mutant protease from said cell or said culture medium.

* * * * *